US006451940B1

United States Patent
Hicks et al.

(10) Patent No.: US 6,451,940 B1
(45) Date of Patent: Sep. 17, 2002

(54) CATALYSTS FOR OLEFIN POLYMERIZATIONS

(75) Inventors: Frederick Hicks, Somerville, MA (US); Maurice S. Brookhart, Chapel Hill, NC (US)

(73) Assignee: E. I. du Pont de Nemours and Company, Wilmington, DE (US)

( * ) Notice: Subject to any disclaimer, the term of this patent is extended or adjusted under 35 U.S.C. 154(b) by 94 days.

(21) Appl. No.: 09/687,195

(22) Filed: Oct. 13, 2000

Related U.S. Application Data

(60) Provisional application No. 60/161,237, filed on Oct. 22, 1999.

(51) Int. Cl.[7] .............................. C08F 4/60; C08F 4/80
(52) U.S. Cl. .................... 526/161; 526/169.1; 526/171; 526/172; 526/308; 526/281; 526/346; 502/117; 502/155; 502/167; 556/148; 556/150; 568/305
(58) Field of Search .............................. 526/161, 169.1, 526/172, 171

(56) References Cited

U.S. PATENT DOCUMENTS 6,060,569 A     5/2000   Bennett et al.
6,127,497 A  * 10/2000   Matsunaga et al. ......... 526/141

FOREIGN PATENT DOCUMENTS

WO     WO 98/30609      7/1998
WO     WO 98/42664     10/1998

OTHER PUBLICATIONS

Dehnen, Stefanie et al., Homoleptic yttrium and lanthanide complexes of aminotroponiminates and aminotroponates: experimental and theoretical studies, J. Chem. Soc., Dalton Trans., 1998, pp. 2425–2429.
Hicks, Frederick A. et al., Synthesis of 2–Anilinotropones via Palladium–Catalyzed Amination of 2–Triflatotropone, Organic Letters, 2000, pp. 219–221, vol. 2, No. 2.
Budarina, Z. N. et al., Intracomplex compounds of nickel, cobalt, and zinc with chelating ligands of the amino(hydroxy)–tropone(thione) series, Koord. Khim., 1981, pp. 409–419, vol. 7, No. 3.
International Search Report PCT/US00/28953 dated Oct. 20, 2000.
Brasen, W. R., N,N'–Disubstituted–1–amino–7–imino–1,3, 5–cycloheptatrienes, a Non–classical Aromatic System, J. Am. Chem. Soc. Japan, 1961, pp. 3125–3135, vol. 83.
Kikuchi, K. et al., The Oxidative Amination of Tropone and Tropolone, Bulletin of the Chemical Society of Japan, 1978, pp. 2338–2341, vol. 51 (8).
Nozoe, T. et al., Reactive Troponoids and o–Aminopheno. I. Synthesis of Cyclohepta[b][1,4]benzoxazine, Bulletin of the Chemical Society of Japan, 1978, pp. 2185–2186, vol. 51 (7).

* cited by examiner

*Primary Examiner*—David W. Wu
*Assistant Examiner*—R. Rabago

(57) ABSTRACT

Selected nickel complexes of the anions of certain 2-aminotropones are olefin polymerization catalysts. Novel 2-aminotropones and their nickel complexes are also disclosed together with methods of making these 2-aminotropones. Suitable complexes have the following structure:

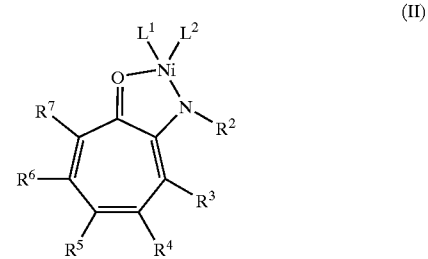

(II)

wherein:

$R^2$ is hydrocarbyl or substituted hydrocarbyl, provided that $R^2$ is attached to said nitrogen atom in (I) by an atom that has at least 2 other atoms that are not hydrogen attached to it; and $R^3$, $R^4$, $R^5$, $R^6$ and $R^7$ are each independently hydrogen, hydrocarbyl, substituted hydrocarbyl or a functional group, provided that any two of $R^3$, $R^4$, $R^5$, $R^6$ and $R^7$ vicinal to one another may form a ring;

$L^1$ is a monodentate monoanionic ligand and $L^2$ is a monodentate neutral ligand or an empty coordination site, or $L^1$ and $L^2$ taken together are a monoanionic bidentate ligand.

11 Claims, No Drawings

CATALYSTS FOR OLEFIN POLYMERIZATIONS

CROSS-REFERENCE TO RELATED APPLICATION

This application claims priority under 35 U.S.C. §119 from U.S. Provisional Application Ser. No. 60/161,237 (filed Oct. 22, 1999), which is incorporated by reference herein for all purposes as if fully set forth.

FIELD OF THE INVENTION

This invention concerns new processes for the polymerization of olefins using as a polymerization catalyst a nickel complex of certain 2-aminotropones. Also described are novel compounds that are the complexes and intermediates for making the complexes, as well as processes for producing such compounds.

TECHNICAL BACKGROUND

Polymers of ethylene and other olefins are important items of commerce, and these polymers are used in a myriad of ways, from low molecular weight polyolefins being used as a lubricant and in waxes, to higher molecular weight grades being used for fiber, films, molding resins, elastomers, etc. In most cases, olefins are polymerized using a catalyst, often a transition metal compound or complex. These catalysts vary in cost per unit weight of polymer produced, the structure of the polymer produced, the possible need to remove the catalyst from the polyolefin, the toxicity of the catalyst, etc. Due to the commercial importance of polymerizing olefins, new polymerization catalysts are constantly being sought.

Arylaminotropones are useful as chemical intermediates, for instance in the synthesis of pharmaceuticals and pesticides.

Nickel complexes of various neutral ligands and monoanionic ligands are known as catalysts for the polymerization of ethylene and other olefins, see for instance (for monoanionic ligands) U.S. Pat. No. 6,060,569, WO9830609 (corresponding to U.S. patent application Ser. No. 09/006536, filed Jan. 13, 1998, now U.S. Pat. No. 6,174,975) and WO9842664, which are incorporated by reference herein for all purposes as if fully set forth. None of these references describe the use of aminotropones as ligands for nickel containing olefin polymerization catalysts.

Anilinotropones, especially 2-anilinotropones, have been made by a variety of methods, see for instance K. Kikuchi, *Bull. Chem. Soc. Jpn.*, vol. 51, p. 2338 (1978); T. Nozoe, *Bull. Chem. Soc. Jpn.*, vol. 51, p. 2185 (1978); and W. R. Brasen, *J. Am. Chem. Soc.*, vol. 83, p. 3125 (1961). The methods described in these references are different from the methods described herein. In addition, yields of the desired 2-anilinotropones are generally lower than reported herein, and/or sterically hindered less basic arylamines are not used in the synthesis thereof.

SUMMARY OF THE INVENTION

One aspect of the present invention concerns a first process for the polymerization of olefins, comprising the step of contacting, at a temperature of about −100° C. to about +200° C., one or more olefins with an active catalyst comprising a nickel complex of an anion of the formula

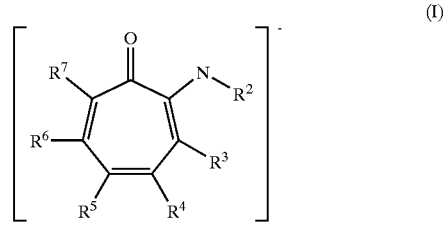

wherein:

$R^2$ is hydrocarbyl or substituted hydrocarbyl, provided that $R^2$ is attached to said nitrogen atom in (I) by an atom that has at least 2 other atoms that are not hydrogen attached to it; and $R^3$, $R^4$, $R^5$, $R^6$ and $R^7$ are each independently hydrogen, hydrocarbyl, substituted hydrocarbyl or a functional group, provided that any two of $R^3$, $R^4$, $R^5$, $R^6$ and $R^7$ vicinal to one another may form a ring.

Another aspect of the present invention concerns a second process for the polymerization of olefins, comprising the step of contacting, at a temperature of about −100° C. to about +200° C., one or more olefins with a compound of the formula

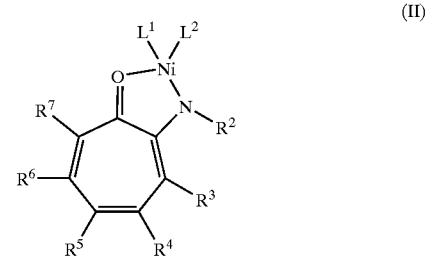

wherein:

$R^2$ is hydrocarbyl or substituted hydrocarbyl, provided that $R^2$ is attached to said nitrogen atom in (I) by an atom that has at least 2 other atoms that are not hydrogen attached to it;

$R^3$, $R^4$, $R^5$, $R^6$ and $R^7$ are each independently hydrogen, hydrocarbyl, substituted hydrocarbyl or a functional group, provided that any two of $R^3$, $R^4$, $R^5$, $R^6$ and $R^7$ vicinal to one another may form a ring;

$L^1$ is a monodentate monoanionic ligand into which an olefin molecule may insert between $L^1$ and the nickel atom, and $L^2$ is an empty coordination site or a monodentate neutral ligand which may be displaced by an olefin, or $L^1$ and $L^2$ taken together are a monoanionicbidentate ligand into which an olefin may insert between said monoanionic bidentate ligand and the nickel atom;

and provided that when $L^1$ and $L^2$ taken together are

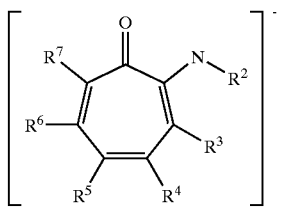
(I)

then a cocatalyst is also present.

In the above-mentioned processes, (II) and/or the nickel complex of (I) may in and of themselves be active catalysts, or may be "activated" by contact with a cocatalyst/activator, as exemplified by the case when $L^1$ and $L^2$ taken together are (I).

The present invention also concerns a compound of the formula

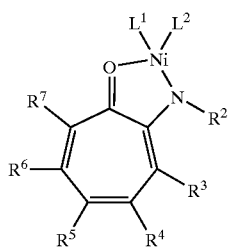
(II)

wherein:
  $R^2$ is hydrocarbyl or substituted hydrocarbyl, provided that $R^2$ is attached to said nitrogen atom in (I) by an atom that has at least 2 other atoms that are not hydrogen attached to it; and
  $R^3$, $R^4$, $R^5$, $R^6$ and $R^7$ are each independently hydrogen, hydrocarbyl, substituted hydrocarbyl or a functional group, provided that any two of $R^3$, $R^4$, $R^5$, $R^6$ and $R^7$ vicinal to one another may form a ring;
  $L^1$ is a monodentate monoanionic ligand, and $L^2$ is a monodentate neutral ligand or an empty coordination site, or $L^1$ and $L^2$ taken together are a monoanionic bidentate ligand.

Another aspect of the present invention is a process for making 2-arylamino substituted tropones, comprising the step of contacting, in solution at a temperature of about 20° C. to about 150° C., a first compound of the formula

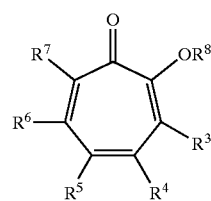
(III)

a second compound of the formula $HNR^9R^{19}$ (IV), a palladium compound, a base capable of deprotonating said second compound, and a third compound which is a mono- or diphosphine in which all of the bonds to phosphorous are to carbon atoms, wherein:
  $R^3$, $R^4$, $R^5$, $R^6$ and $R^7$ are each independently hydrogen, hydrocarbyl, substituted hydrocarbyl or a functional group, provided that any two of $R^3$, $R^4$, $R^5$, $R^6$ and $R^7$ vicinal to one another may form a ring;
  $R^8$ is a group such that the conjugate acid of $-OR^8$ has a pKa of <0 in water at 20° C.;
  $R^{19}$ is hydrocarbyl, substituted hydrocarbyl or hydrogen; and
  $R^9$ is aryl or substituted aryl.

Still another aspect of the present invention is a compound of the formula

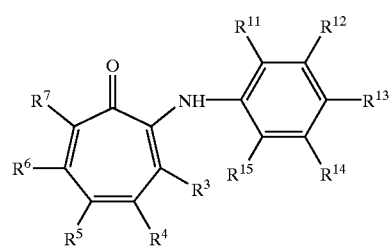
(X)

wherein:
  $R^3$, $R^4$, $R^5$, $R^6$ and $R^7$ are each independently hydrogen, hydrocarbyl, substituted hydrocarbyl or a functional group, provided that any two of $R^3$, $R^4$, $R^5$, $R^6$ and $R^7$ vicinal to one another may form a ring; and
  $R^{11}$, $R^{12}$, $R^{13}$, $R^{14}$ and $R^{15}$ are each independently hydrogen, hydrocarbyl substituted hydrocarbyl or a functional group, provided that any two of $R^{11}$, $R^{12}$, $R^{13}$, $R^{14}$ and $R^{15}$ vicinal to one another taken together may form a ring; provided that:
  both of $R^{11}$ and $R^{15}$ are not hydrogen; and/or
  the total of the Hammett a constants for $R^{11}$, $R^{12}$, $R^{13}$, $R^{14}$ and $R^{15}$ is about 0.50 or more; and/or
  an $E_S$ for one or both of $R^{11}$ and $R^{15}$ is −0.10 or less.

A further aspect of the present invention is an anion of the formula

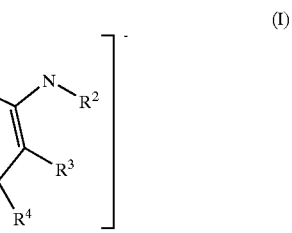
(I)

wherein:
  $R^2$ is hydrocarbyl or substituted hydrocarbyl, provided that $R^2$ is attached to said nitrogen atom in (I) by an atom that has at least 2 other atoms that are not hydrogen attached to it; and
  $R^3$, $R^4$, $R^5$, $R^6$ and $R^7$ are each independently hydrogen, hydrocarbyl, substituted hydrocarbyl or a functional group, provided that any two of $R^3$, $R^4$, $R^5$, $R^6$ and $R^7$ vicinal to one another may form a ring.

DETAILED DESCRIPTION OF THE PREFERRED EMBODIMENTS

Herein, certain terms are used. Some of them are:

A "hydrocarbyl group" is a univalent group containing only carbon and hydrogen. As examples of hydrocarbyls may be mentioned unsubstituted alkyls, cycloalkyls and aryls. If not otherwise stated, it is preferred that hydrocarbyl groups herein contain 1 to about 30 carbon atoms.

By "substituted hydrocarbyl" herein is meant a hydrocarbyl group that contains one or more substituent groups which are inert under the process conditions to which the compound containing these groups is subjected. The substituent groups also do not substantially interfere with the process. If not otherwise stated, it is preferred that substituted hydrocarbyl groups herein contain 1 to about 30 carbon atoms. Included in the meaning of "substituted" are heteroaromatic rings. When a heteroaromatic ring is present, it may be attached to another group through the heteroatom. In substituted hydrocarbyl all of the hydrogens may be substituted, as in trifluoromethyl.

By "(inert) functional group" herein is meant a group other than hydrocarbyl or substituted hydrocarbyl which is inert under the process conditions to which the compound containing the group is subjected. The functional groups also do not substantially interfere with any process described herein that the compound in which they are present may take part in. Examples of functional groups include halo (fluoro, chloro, bromo and iodo), ether such as —OR$^{22}$ wherein R$^{22}$ is hydrocarbyl or substituted hydrocarbyl. In cases in which the functional group may be near a nickel atom the functional group should not coordinate to the metal atom more strongly than the groups in those compounds are shown as coordinating to the metal atom, that is they should not displace the desired coordinating group.

By "olefin" is meant a compound containing one or more olefinic double bonds. In the event that the compound contains more than one olefinic double bond, they should be non-conjugated. As examples of olefins may be mentioned cyclopentene, a styrene, a norbornene, and compounds of the formulas R$^{17}$CH=CH$_2$ wherein R$^{17}$ is hydrogen or alkyl.

By an oligomerization or polymerization "co-catalyst" or "catalyst activator" is meant a compound that reacts with a transition metal compound to form an activated catalyst species. A preferred catalyst activator is an "alkyl aluminum compound", that is, a compound which has at least one alkyl group bound to an aluminum atom. Other groups such as alkoxide, hydride, and halogen may also be bound to aluminum atoms in the compound.

By "neutral Lewis base" is meant a compound, which is not an ion, that can act as a Lewis base. Examples of such compounds include ethers, amines, sulfides, and organic nitriles.

By "neutral Lewis acid" is meant a compound, which is not an ion, that can act as a Lewis acid. Examples of such compounds include boranes, alkylaluminum compounds, aluminum halides, and antimony [V] halides.

By "cationic Lewis acid" is meant a cation that can act as a Lewis acid. Examples of such cations are sodium and silver cations.

By an "empty coordination site" is meant a potential coordination site on a metal atom that does not have a ligand bound to it. Thus if an olefin molecule (such as an ethylene molecule) is in the proximity of the empty coordination site, the olefin molecule may coordinate to the metal atom.

By a "ligand into which an olefin molecule may insert" between the ligand and a nickel atom is meant a ligand coordinated to the nickel atom into which an olefin molecule or a coordinated olefin molecule (such as an ethylene molecule or a coordinated ethylene molecule) may insert to start or continue a polymerization. For instance, this may take the form of the reaction (wherein L is a ligand):

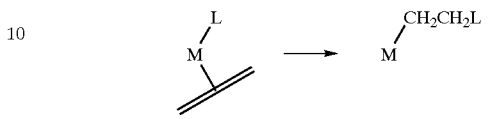

By a "ligand which may be displaced by an olefin" is meant a ligand coordinated to a transition metal, which when exposed to an olefin (such as ethylene) is displaced as the ligand by the olefin.

By a "monoanionic ligand" is meant a ligand with one negative charge.

By a "neutral ligand" is meant a ligand that is not charged. "Alkyl group" and "substituted alkyl group" have their usual meaning (see above for substituted under substituted hydrocarbyl). Unless otherwise stated, alkyl groups and substituted alkyl groups preferably have 1 to about 30 carbon atoms.

By a "styrene" herein is meant a compound of the formula

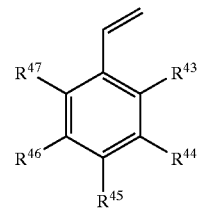

(XXXIV)

wherein R$^{43}$, R$^{44}$, R$^{45}$, R$^{46}$ and R$^{47}$ are each independently hydrogen, hydrocarbyl, substituted hydrocarbyl or a functional group, all of which are inert in the polymerization process. It is preferred that all of R$^{43}$, R$^{44}$, R$^{45}$, R$^{46}$ and R$^{47}$ are hydrogen. Styrene (itself) is a preferred styrene.

By a "norbornene" is meant ethylidene norbornene, dicyclopentadiene, or a compound of the formula

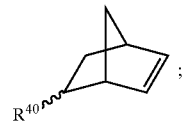

(XXXV)

wherein R$^{40}$ is hydrogen or hydrocarbyl containing 1 to 20 carbon atoms. It is preferred that R$^{40}$ is hydrogen or alkyl, more preferably hydrogen or n-alkyl, and especially preferably hydrogen. The norbornene may be substituted by one or more hydrocarbyl, substituted hydrocarbyl or functional groups in the R$^{40}$ or other positions, with the exception of the vinylic hydrogens, which remain. Norbornene (itself), dimethyl endo-norbornene-2,3-dicarboxylate, t-butyl 5-norbornene-2-carobxylate are preferred norbornenes and norbornene (itself) is especially preferred.

By a "π-allyl group" is meant a monoanionic ligand with 3 adjacent sp$^2$ carbon atoms bound to a metal center in an η$^3$ fashion. The three sp² carbon atoms may be substituted with other hydrocarbyl groups or functional groups.

By "aryl" is meant a monovalent aromatic group in which the free valence is to the carbon atom of an aromatic ring. An aryl may have one or more aromatic rings which may be fused, connected by single bonds or other groups.

By "substituted aryl" is meant a monovalent aromatic group substituted as set forth in the above definition of "substituted hydrocarbyl". Similar to an aryl, a substituted aryl may have one or more aromatic rings which may be fused, connected by single bonds or other groups; however, when the substituted aryl has a heteroaromatic ring, the free valence in the substituted aryl group can be to a heteroatom (such as nitrogen) of the heteroaromatic ring instead of a carbon.

The polymerizations herein are carried out by a nickel complex of anion (I). In (I), and in all complexes and compounds containing (I) or its parent conjugate acid, it is preferred that:

$R^3$, $R^4$, $R^5$, $R^6$ and $R^7$ are all hydrogen; and/or $R^2$ is aryl or substituted aryl, especially phenyl or substituted phenyl.

Useful groups for $R^2$ include, for example

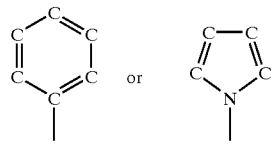

which may be substituted in any or all of their ring positions. It is preferred that at least one position next to (ortho) the free valence of the aryl ring be substituted, and more preferred that both of these positions be substituted. In particular it is more preferred that $R^2$ is (VI)

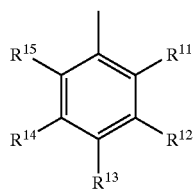

wherein each of $R^{11}$, $R^{12}$, $R^{13}$, $R^{14}$ and $R^{15}$ are independently hydrogen, hydrocarbyl substituted hydrocarbyl or a functional group, provided that any two of $R^{11}$, $R^{12}$, $R^{13}$, $R^{14}$ and $R^{15}$ vicinal to one another taken together may form a ring. In one particularly preferred form both $R^{11}$ and $R^{15}$ are not hydrogen, and/or $R^{12}$, $R^{13}$ and $R^{14}$ are hydrogen. In another preferred form $R^{11}$ and $R^{15}$ are each independently chosen from the group consisting of alkyl containing 1 to 6 carbon atoms, perfluoroalkyl, alkoxy, phenyl and halo, more preferably alkyl containing 1 to 4 carbon atoms, phenyl and halo. Particularly preferred are when $R^{11}$ and $R^{13}$ are both i-propyl or phenyl, or when $R^{11}$ is methyl and $R^{15}$ is trifluoromethyl. Preferred specific groups (VI) are shown in Table 1.

TABLE 1

| $R^{11}$ | $R^{12}$ | $R^{13}$ | $R^{14}$ | $R^{15}$ |
|---|---|---|---|---|
| Me | H | H | H | Me |
| IPr | H | H | H | iPr |
| TBu | H | H | H | H |
| TBu | H | H | H | Me |
| Cl | H | H | H | Cl |
| Br | H | H | H | Br |
| F | F | F | F | F |
| H | CF₃ | H | CF₃ | H |
| Ph | H | H | H | Ph |
| F | H | H | H | F |

All of the complexes of (I) can be made from the corresponding tropone (VII)

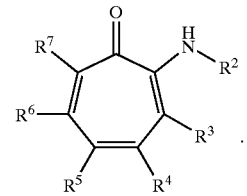

In turn (VII) can be made by the process described below, using a palladium catalyst in the presence of a phosphine compound.

In a process to make (VII) the appropriately substituted arylamine, (IV) (and preferred substitution is the same as in (I)), is reacted with an appropriately substituted tropone ester (and preferred substitution is as in (I)), in the presence of a base, a palladium compound and a mono- or diphosphine. This reaction is carried out in solution, although not all of the ingredients must be totally soluble at all times, all of the starting materials, except the base, should be at least somewhat soluble. Preferred solvents are relatively inert to all of the ingredients and products, and include hydrocarbon solvents such as toluene, and ethers such as 1,4-dioxane, ethyl ether and tetrahydrofuran.

The palladium compound may be a Pd[II] compound or a Pd[0] compound, such as palladium acetate, PdX₂ wherein each X is independently halogen, and palladium bis (dibenzylideneacetone), which is preferred. The phosphine may be a mono- or diphosphine in which all three of the bonds to phosphorous are to separate carbon atoms. It is preferred that the phosphine be somewhat sterically hindered. Useful phosphines include (o-tolyl)₃P, (t-Bu)₃P, 1,1'-bis(diphenylphosphino)ferrocene, bis(2-diphenylphosphinophenyl)ether, 2-(di-t-butylphosphino) biphenyl, 2-(dicylohexylphosphino)biphenyl, and

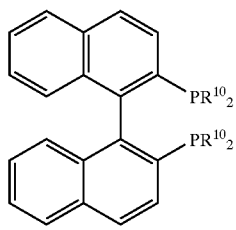

(XI)

wherein each $R^{10}$ is independently aryl or substituted aryl and preferably all of $R^{10}$ are phenyl (this compound is sometimes abbreviated "BINAP"). A preferred phosphine is (XI).

The base may be any metal salt, preferably an alkali metal salt, which can serve as an acceptor for the proton liberated from the arylamine during the process. The base should have at least sparing solubility in the process solvent. Useful bases include alkali metal carbonates such as cesium carbonate, alkali metal phosphates such as potassium phosphate ($K_3PO_4$), alkali metal alkoxides such as potassium t-butoxide, and alkali metal amides such as sodium hexamethyldisilamide.

In the process to make (VII) ratios of the various ingredients are not critical, but to make efficient and economical use of the various ingredients, it is preferred that:

the molar ratio of (III):(IV) is about 0.1 to about 1.0, more preferably about 0.8 to about 0.9;

the amount of gram-atoms of palladium (in whatever form the Pd is added) is about 0.01 to about 10 percent of the number of moles of tropone, more preferably about 0.5 to 1.5 percent; and/or the number of equivalents of base to moles of tropone is preferably about 1.0 to about 4.0, more preferably about 1.2 to about 1.6.

The process to make (VII) is preferably carried out at a temperature of about 20° C. to about 150° C., more preferably about 50° C. to about 120° C., and especially preferably about 70° C. to about 90° C. It is preferred to carry out the process in the absence of water (and other active hydrogen compounds) and oxygen, especially in the absence of oxygen. This is conveniently carried done by carrying out the process under an inert gas such as nitrogen or argon. The time required for this process is also not critical, 3 to 48 hours, more typically 12–15 hours, being useful ranges.

In the process to make (VII), (III) is one of the starting materials. In (III), $R^8$ is a group such that the conjugated acid of $R^8O$— has a pKa of <0. Useful groups for $R^8$ include $R^{16}SO_2$—, wherein $R^{16}$ is perfluorohydrocarbyl, especially perfluoroalkyl, and p-tolyl. A preferred group for $R^8$ is $R^{16}SO_2$—, wherein $R^{16}$ is perfluoroalkyl, especially trifluoromethyl (sometimes called the "triflate" group). (III) may be made by methods known in the art, for instance the preparation of 2-triflatotropone is found in A. M. Echavarren, et al., *J. Am. Chem. Soc.*, vol. 110, p. 1557 (1988), which is included by reference herein.

The process to make (VII) (and hence (X)) herein produces these types of compounds in improved yields and/or allows the production of compounds which cannot be produced by simple nucleophilic displacements, for instance using aromatic amines (IV) in which the amine group is sterically hindered by substitution at one or both of the ortho positions, and/or the amine has reduced bascisity because the aromatic group bears electron withdrawing substituents.

In (IV) (and in any of the arylaminotropones subsequently produced) it is preferred that $R^{19}$ is alkyl, substituted alkyl or hydrogen, more preferred that it is alkyl or hydrogen, and especially preferred that it is hydrogen.

The steric effect of various groupings has been quantified by a parameter called $E_S$, see R. W. Taft, Jr., *J. Am. Chem. Soc.*, vol. 74, p. 3120–3128 (1952), and M. S. Newman, *Steric Effects in Organic Chemistry*, John Wiley & Sons, New York, 1956, p. 598–603, both of which are hereby incorporated by reference herein for all purposes as if fully set forth. For the purposes herein, the $E_S$ values are those for o-substituted benzoates described in these publications. If the value for $E_S$ for any particular group is not known, it can be determined by methods described in these publications. For the purposes herein, the value of hydrogen is defined to be the same as for methyl (0.00). Representative values for $E_S$ are (taken from Table V in Taft and Series 2-2 through 2-10 in Newman) —$OCH_3$ +0.97, —Br +0.01, —I −0.20, $CH_3CH_2$— 0.07, $CH_3CH_2CH_2$— −0.36, i-$C_3H_7$— −0.47, t-$C_4H_9$— −1.54, $C_6H_5$— −0.90. In one preferred form of (X) the $E_S$ for either of the ortho substituents is −0.10 or less, preferably about −0.25 or less, and especially preferably about −0.50 or less.

Another preferred form of (X) is when the phenyl ring has electron withdrawing groups attached to it. The electron withdrawing ability of various substituents may be measured by the Hammett constant, see for instance H. H. Jaffe, *Chem. Rev.*, vol. 53, p. 191–261 (1953), especially Table 7, which is hereby included by reference. Since Hammett substituents constants are often not calculated for ortho substituents, for any ortho substituent the Hammett constant will be taken as the Hammett para constant ($\sigma_{para}$). The total of all the $\sigma$ constants for all of the substituents on the phenyl ring is about 0.50 or more, more preferably about 0.75 or more.

It is also preferred in (I) (and in compounds in which it occurs) that provided that one or more of the following obtains: both of $R^{11}$ and $R^{15}$ are not hydrogen; the total of the Hammett $\sigma$ constants for $R^{11}$, $R^{12}$, $R^{13}$, $R^{14}$ and $R^{15}$ is about 0.50 or more; and an $E_S$ for one or both of $R^{11}$ and $R^{15}$ is −0.10 or less. The more preferred forms for (X) are also preferred in (I).

Herein (VII) may be converted to a nickel complex such as (II), and in turn (II) may be active in and of itself and thus useful directly as an olefin polymerization catalyst, or may be converted to an active polymerization catalyst by contact with one or more other compounds (so-called cocatalysts). Thus (VII) may be converted to its anion by reaction with a strong base such as sodium hydride, and this anion (which is actually (I)) may be reacted with an appropriate nickel compound to form (II). Useful nickel compounds include:

$(Ph_3P)_2Ni(Ph)(Cl)$ (see Example 13) which gives (II) in which $L^1$ is Ph, and $L^2$ is $Ph_3P$;

$(TMEDA)_2Ni(Ph)(Cl)$ in the presence of a "trapping ligand" $L^2$ such as pyridine, which specifically gives (IX) for instance in which $L^1$ is Ph, and $L^2$ is pyridine;

$(Ph_3P)_2NiCl_2$ which gives (II) in which $L^1$ is Cl, and $L^2$ is $Ph_3P$; and $((allyl)Ni(X))_2$ which gives (II) in which $L^1$ and $L^2$ taken together are π-allyl.

Methods of synthesis of these types of nickel complexes may also be found in previously incorporated U.S. Pat. No.

6,060,569, WO98/30609 and WO98/42664, and R. H. Grubbs., et al., *Organometallics*, vol. 17, p. 3149 (1988), which is also incorporated by reference herein for all purposes as if fully set forth.

In (II) useful groups $L^1$ include halide (especially chloride), hydrocarbyl and substituted hydrocarbyl especially phenyl and alkyl and particularly phenyl, methyl, hydride and acyl. Useful groups for $L^2$ include phosphine such as triphenylphosphine, nitrile such as acetonitrile, ethers such as ethyl ether, pyridine, and tertiary alkylamines such as TMEDA (N,N,N',N'-tetramethyl-1,2-ethylenediamine). Alternatively $L^1$ and $L^2$ taken together may be a π-allyl or π-benzyl group such as

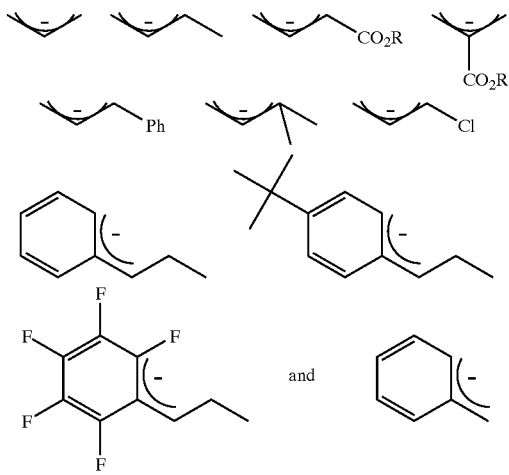

wherein R is hydrocarbyl.

In (II) when an olefin (such as ethylene) may insert between $L^1$ and the nickel atom, and $L^2$ is an empty coordination site or is a ligand which may be displaced by an olefin (such as ethylene), or $L^1$ and $L^2$ taken together are a bidentate monoanionic ligand into which an olefin (such as ethylene) may be inserted between that ligand and the nickel atom, (II) may by itself catalyze the polymerization of an olefin. Examples of $L^1$ into which an olefin (and particularly ethylene) may insert between it an the nickel atom are hydrocarbyl and substituted hydrocarbyl especially phenyl and alkyl and particularly methyl, hydride and acyl, and ligands $L^2$ which an olefin (and particularly ethylene) may displace include phosphine such as triphenylphosphine, nitrile such as acetonitrile, ether such as ethyl ether, pyridine, and tertiary alkylamines such as TMEDA. Ligands in which $L^1$ and $L^2$ taken together are a bidentate monoanionic ligand into which an olefin (and particularly ethylene) may insert between that ligand and the nickel atom include π-allyl- or π-benzyl-type ligands (in this instance, sometimes it may be necessary to add a neutral Lewis acid cocatalyst such as triphenylborane to initiate the polymerization, see for instance previously incorporated WO98/30609). For a summary of which ligands an olefin (and particularly ethylene) may insert into (between) the ligand and nickel atom) see for instance J. P. Collman, et al., *Principles and Applications of Organotransition Metal Chemistry*, University Science Book, Mill Valley, Calif., 1987, included herein by reference. If for instance $L^1$ is not a ligand into which an olefin (such as ethylene) may insert between it and the nickel atom, it may be possible to add a cocatalyst which may convert $L^1$ into a ligand which will undergo such an insertion. Thus if $L^1$ is halo such as chloride or bromide, or carboxylate, it may be converted to hydrocarbyl such as alkyl by use of a suitable alkylating agent such as an alkylaluminum compound, a Grignard reagent or an alkyllithium compound. It may be converted to hydride by used of a compound such as sodium borohydride.

In (II) when $L^1$ and $L^2$ taken together are (I), in the polymerizations a cocatalyst (sometimes also called an activator) which is an alkylating or hydriding agent is also present in the olefin polymerization. It is preferred however that $L^1$ and $L^2$ taken together are not (I). A preferred cocatalyst is an alkylaluminum compound, and particularly preferred are trialkylaluminum compound such as trimethylaluminum, triethylaluminum and tri-i-butylaluminum, and trimethylaluminum is especially preferred. More than one such cocatalyst may be used in combination.

In the polymerizations herein homo- or copolymers of the various olefins may be produced. A preferred olefin (or combination of olefins) is $R^{17}CH=CH_2$ wherein $R^{17}$ is hydrogen or n-alkyl containing 1 to 15 carbon atoms, and especially preferred is when $R^{17}$ is hydrogen or methyl (ethylene or propylene, respectively), and more preferred is when $R^{17}$ is hydrogen (ethylene).

In the polymerization processes herein, the temperature at which the polymerization is carried out is about −100° C. to about +200° C., preferably about −60° C. to about 150° C., more preferably about −20° C. to about 100° C. The pressure of the olefin (if it is a gas) at which the polymerization is carried out is not critical, atmospheric pressure to about 275 MPa being a suitable range. Generally speaking the response of the catalyst, and hence the polymer produced, to the effects of temperature and pressure are similar to other nickel catalysts, see for instance U.S. Pat. No. 5,880,241 (incorporated by reference herein for all purposes as if fully set forth). As shown in Table 3 as the temperature increases catalyst productivity increases until about 80° C. (at least under these particular polymerization conditions and this catalyst) and then starts decreasing, and the branching level increases as the temperature increases. Up to a point at least, increasing the ethylene pressure (Table 4) increases catalyst productivity, decreases branching, and increases polymer molecular weight. It is also believed that as the ethylene pressure increases, it becomes more important that the ethylene used be of high purity. The effect of catalyst loading (Table 5) is somewhat uncertain since in Example 54 there was a large exotherm.

The polymerization processes herein may be run in the presence of various liquids, particularly aprotic organic liquids. The catalyst system, monomer(s), and polymer may be soluble or insoluble in these liquids, but obviously these liquids should not prevent the polymerization from occurring. Suitable liquids include alkanes, cycloalkanes, selected halogenated hydrocarbons and aromatic hydrocarbons. Specific useful solvents include hexane, toluene, benzene, chlorobenzene, tetrahydrofuran, methylene chloride and 1,2,4-trichlorobenzene. The effects of various solvents on the polymerizations are shown in Table 7.

Various polar compounds such as ethyl acetate, triethylamine, water and ethanol may be present in the polymerization, although in some instances the yields may be reduced (see Table 6). The polymerization may also be carried out in the presence of air. It is noted that the polymerization proceeds with some of these additives even though they may contain active hydrogen atoms (water, ethanol).

The olefin polymerizations herein may also initially be carried out in the "solid state" by, for instance, supporting the nickel compound on a substrate such as silica or alumina, activating if necessary it with one or more cocatalysts and contacting it with the olefin(s). Alternatively, the support may first be contacted (reacted) with a cocatalyst (if needed) such as an alkylaluminum compound, and then contacted with an appropriate Ni compound. The support may also be able to take the place of a Lewis or Bronsted acid, for instance, an acidic clay such as montmorillonite, if needed. Another method of making a supported catalyst is to start a polymerization or at least make a nickel complex of another olefin or oligomer of an olefin such as cyclopentene on a support such as silica or alumina. These "heterogeneous" catalysts may be used to catalyze polymerization in the gas phase or the liquid phase. By gas phase is meant that a gaseous olefin is transported to contact with the catalyst particle.

In all of the polymerization processes described herein oligomers and polymers of the various olefins are made. They may range in molecular weight from oligomeric olefins, to lower molecular weight oils and waxes, to higher molecular weight polyolefins. One preferred product is a polymer with a degree of polymerization (DP) of about 10 or more, preferably about 40 or more. By "DP" is meant the average number of repeat (monomer) units in a polymer molecule.

Depending on their properties, the polymers made by the processes described herein are useful in many ways. For instance if they are thermoplastics, they may be used as molding resins, for extrusion, films, etc. If they are elastomeric, they may be used as elastomers. If they contain functionalized monomers such as acrylate esters, they are useful for other purposes, see for instance previously incorporated U.S. Pat. No. 5,880,241.

Depending on the process conditions used and the polymerization catalyst system chosen, polymers, even those made from the same monomer(s) may have varying properties. Some of the properties which may change are molecular weight and molecular weight distribution, crystallinity, melting point, and glass transition temperature. Except for molecular weight and molecular weight distribution, branching can affect all the other properties mentioned, and branching may be varied (using the same nickel compound) using methods described in previously incorporated U.S. Pat. No. 5,880,241.

It is known that blends of distinct polymers, that vary for instance in the properties listed above, may have advantageous properties compared to "single" polymers. For instance it is known that polymers with broad or bimodal molecular weight distributions may be melt processed (be shaped) more easily than narrower molecular weight distribution polymers. Thermoplastics such as crystalline polymers may often be toughened by blending with elastomeric polymers.

Therefore, methods of producing polymers which inherently produce polymer blends are useful especially if a later separate (and expensive) polymer mixing step can be avoided. However in such polymerizations one should be aware that two different catalysts may interfere with one another, or interact in such a way as to give a single polymer.

In such a process the Ni containing polymerization catalyst disclosed herein can be termed the first active polymerization catalyst. Monomers useful with these catalysts are those described (and also preferred) above. A second active polymerization catalyst (and optionally one or more others) is used in conjunction with the first active polymerization catalyst. The second active polymerization catalyst may be another late transition metal catalyst, for example as described in previously incorporated WO98/30609, U.S. Pat. No. 5,880,241 and U.S. Pat. No. 6,060,569, as well as in U.S. Pat. No. 5,714,556 and U.S. Pat. No. 5,955,555, which are also incorporated by reference herein for all purposes as if fully set forth.

Other useful types of catalysts may also be used for the second active polymerization catalyst. For instance so-called Ziegler-Natta and/or metallocene-type catalysts may also be used. These types of catalysts are well known in the polyolefin field, see for instance *Angew. Chem.*, Int. Ed. Engl., vol. 34, p. 1143–1170 (1995), EP-A-0416815 and U.S. Pat. No. 5,198,401 for information about metallocene-type catalysts, and J. Boor Jr., *Ziegler-Natta Catalysts and Polymerizations*, Academic Press, New York, 1979 for information about Ziegler-Natta-type catalysts, all of which are incorporated by reference herein for all purposes as if fully set forth. Many of the useful polymerization conditions for all of these types of catalysts and the first active polymerization catalysts coincide, so conditions for the polymerizations with first and second active polymerization catalysts are easily accessible. Oftentimes the "co-catalyst" or "activator" is needed for metallocene or Ziegler-Natta-type polymerizations. In many instances the same compound, such as an alkylaluminum compound, may be used as an "activator" for some or all of these various polymerization catalysts.

In one preferred process described herein the first olefin(s) (the monomer(s) polymerized by the first active polymerization catalyst) and second olefin(s) (the monomer(s) polymerized by the second active polymerization catalyst) are identical, and preferred olefins in such a process are the same as described immediately above. The first and/or second olefins may also be a single olefin or a mixture of olefins to make a copolymer. Again it is preferred that they be identical particularly in a process in which polymerization by the first and second active polymerization catalysts make polymer simultaneously.

In some processes herein the first active polymerization catalyst may polymerize a monomer that may not be polymerized by said second active polymerization catalyst, and/or vice versa. In that instance two chemically distinct polymers may be produced. In another scenario two monomers would be present, with one polymerization catalyst producing a copolymer, and the other polymerization catalyst producing a homopolymer, or two copolymers may be produced which vary in the molar proportion or repeat units from the various monomers. Other analogous combinations will be evident to the artisan.

In another variation of this process one of the polymerization catalysts makes an oligomer of an olefin, preferably ethylene, which oligomer has the formula $R^{70}CH=CH_2$, wherein $R^{70}$ is n-alkyl, preferably with an even number of carbon atoms. The other polymerization catalyst in the process them (co)polymerizes this olefin, either by itself or preferably with at least one other olefin, preferably ethylene, to form a branched polyolefin. Preparation of the oligomer (which is sometimes called an α-olefin) by a second active polymerization-type of catalyst can be found in previously incorporated U.S. Pat. No. 5,880,241 as well as U.S. Pat. No. 6,103,946 (also incorporated by reference for all purposes as if fully set forth).

Likewise, conditions for such polymerizations, using catalysts of the second active polymerization type, will also be found in the appropriate above mentioned references.

Two chemically different active polymerization catalysts are used in this polymerization process. The first active polymerization catalyst is described in detail above. The second active polymerization catalyst may also meet the limitations of the first active polymerization catalyst, but must be chemically distinct. For instance, it may have a different transition metal present, and/or utilize a different type of ligand and/or the same type of ligand which differs in structure between the first and second active polymerization catalysts. In one preferred process, the ligand type and the metal are the same, but the ligands differ in their substituents.

Included within the definition of two active polymerization catalysts are systems in which a single polymerization catalyst is added together with another ligand, preferably the same type of ligand, which can displace the original ligand coordinated to the metal of the original active polymerization catalyst, to produce in situ two different polymerization catalysts.

The molar ratio of the first active polymerization catalyst to the second active polymerization catalyst used will depend on the ratio of polymer from each catalyst desired, and the relative rate of polymerization of each catalyst under the process conditions. For instance, if one wanted to prepare a "toughened" thermoplastic polyethylene that contained 80% crystalline polyethylene and 20% rubbery polyethylene, and the rates of polymerization of the two catalysts were equal, then one would use a 4:1 molar ratio of the catalyst that gave crystalline polyethylene to the catalyst that gave rubbery polyethylene. More than two active polymerization catalysts may also be used if the desired product is to contain more than two different types of polymer.

The polymers made by the first active polymerization catalyst and the second active polymerization catalyst may be made in sequence, i.e., a polymerization with one (either first or second) of the catalysts followed by a polymerization with the other catalyst, as by using two polymerization vessels in series. However it is preferred to carry out the polymerization using the first and second active polymerization catalysts in the same vessel(s), i.e., simultaneously. This is possible because in most instances the first and second active polymerization catalysts are compatible with each other, and they produce their distinctive polymers in the other catalyst's presence. Any of the processes applicable to the individual catalysts may be used in this polymerization process with 2 or more catalysts, i.e., gas phase, liquid phase, continuous, etc.

Catalyst components which include Ni complexes of (I), with or without other materials such as one or more cocatalysts and/or other polymerization catalysts are also disclosed herein. For example, such a catalyst component could include the Ni complex supported on a support such as alumina, silica, a polymer, magnesium chloride, sodium chloride, etc., with or without other components being present. It may simply be a solution of the Ni complex, or a slurry of the Ni complex in a liquid, with or without a support being present.

The polymers produced by this process may vary in molecular weight and/or molecular weight distribution and/ or melting point and/or level of crystallinity, and/or glass transition temperature and/or other factors. For copolymers the polymers may differ in ratios of comonomers if the different polymerization catalysts polymerize the monomers present at different relative rates. The polymers produced are useful as molding and extrusion resins and in films as for packaging. They may have advantages such as improved melt processing, toughness and improved low temperature properties.

Hydrogen or other chain transfer agents such as silanes (for example trimethylsilane or triethylsilane) may be used to lower the molecular weight of polyolefin produced in the polymerization process herein. It is preferred that the amount of hydrogen present be about 0.01 to about 50 mole percent of the olefin present, preferably about 1 to about 20 mole percent. When liquid monomers (olefins) are present, one may need to experiment briefly to find the relative mounts of liquid monomers and hydrogen (as a gas). If both the hydrogen and monomer(s) are gaseous, their relative concentrations may be regulated by their partial pressures.

In the Examples, all pressures are gauge pressures. Branching was determined by $^1H$ NMR, taking the total of the methyl carbon atoms as the number of branches. Branching is uncorrected for end groups. The following abbreviations are used:

BINAP—see compound (XI)
dba—dibenzylideneacetone
EtOAc—ethyl acetate
EtOH—ethanol
Mn—number average molecular weight
Mp—melting point
$NEt_3$—triethylamine
PDI—weight average molecular weight/number average molecular weight
PhCl—chlorobenzene
RT—room temperature
THF—tetrahydrofuran
Tm—melting point

EXAMPLES 1–11

Preparation of 2-Anilinotropones
General Procedure A—The Conversion of 2-Triflatotropone to 2-Anilinotropones with Liquid Anilines A Schlenk tube, flame-dried in vacuo, was placed under an Ar atmosphere on a vacuum line. The tube was charged with Pd$_2$(dba)$_3$ (5 mg, 0.005 mmol), rac-BINAP (7 mg, 0.01 mmol), Cs$_2$CO$_3$ (456 mg, 1.4 mmol), and 2-triflatotropone (254 mg, 1.0 mmol). Toluene (2 mL) was added followed by the appropriate aniline (1.2 mmol). The Schlenk tube was sealed and heated to 80° C. for approximately 12 h. The reaction mixture was allowed to cool to RT, filtered through a pad of silica gel with the aid of ethyl ether (100 mL), and concentrated to afford the crude product. Purification was effected via flash column chromatography on silica gel.
General Procedure B—The Conversion of 2-Triflatotropone to 2-Anilinotropones with Solid Anilines A Schlenk tube, flame-dried in vacuo, was placed under an Ar atmosphere on a vacuum line. The tube was charged with Pd$_2$(dba)$_3$ (5 mg, 0.005 mmol), rac-BINAP (7 mg, 0.01 mmol), Cs$_2$CO$_3$ (456 mg, 1.4 mmol), 2-triflatotropone (254 mg, 1.0 mmol), and the appropriate aniline (1.2 mmol). Toluene (2 mL) was added and the Schlenk tube was sealed and heated to 80° C. for approximately 12 h. The reaction mixture was allowed to cool to RT, filtered through a pad of silica gel with the aid of ethyl ether (100 mL), and concentrated to afford the crude product. Purification was effected via flash column chromatography on silica gel.

The individual Examples 1–11 below give the aniline used to produce the corresponding 2-anilinotropone (substitution patter on the phenyl rings remained the same).

EXAMPLE 1

General procedure A was used to convert 2,6-dimethylaniline (148 μl, 1.2 mmol) to the desired product in 15 h. Purification via flash column chromatography (eluants 3:2 hexane:ether) afforded 201 mg (90% yield) of an orange solid. Mp: 76–78° C. $^1$H NMR (250 MHz, CDCl$_3$): δ 8.40 (bs, 1H); 7.32 (m, 2H); 7.18 (m, 3H); 7.08 (t, J=10.5 Hz, 1H); 6.73 (m, 1H); 6.22 (d, J=10.5 Hz, 1H); 2.15 (s, 6H). $^{13}$C NMR (100 MHz, CDCl$_3$): δ 176.6, 154.6, 137.3, 136.3, 136.2, 135.1, 129.9, 128.7, 127.8, 123.5, 109.6, 18.0. Anal. Calcd for C$_{15}$H$_{15}$NO: C, 79.97; H, 6.71; N, 6.22. Found: C, 79.92; H, 6.71; N, 6.05.

EXAMPLE 2

General procedure A was used to convert 2,6-di-i-propylaniline (227 μl, 1.2 mmol) to the desired product in 14 h. Purification via flash column chromatography (eluants 2:1 hexane:ether) afforded 242 mg (86% yield) of an orange solid. Mp: 86–88° C. $^1$H NMR (200 MHz, CDCl$_3$): δ 8.42 (bs, 1H); 7.43–7.24 (m, 5H); 7.06 (t, J=10.2 Hz, 1H); 6.71 (m, 1H); 6.26 (d, J=10.2 Hz, 1H); 2.90 (m, 2H); 1.15 (d, J=7.0 Hz, 6H); 1.11 (d, J=7.0 Hz, 6H). $^{13}$C NMR (100 MHz, CDCl$_3$): δ 176.5, 156.4, 146.9, 137.5, 136.2, 132.5, 130.0, 128.9, 124.4, 123.6, 110.4, 28.6, 24.6, 23.4. Anal. Calcd for C$_{19}$H$_{23}$NO: C, 81.10; H, 8.24; N, 4.98. Found: C, 81.15; H, 8.20; N, 4.94.

EXAMPLE 3

General procedure A was used to convert 2-t-butylaniline (187 μl, 1.2 mmol) to the desired product in 16 h. Purification via flash column chromatography (eluants 3:1 hexane:ether) afforded 221 mg (88% yield) of an orange solid. Mp: 92–94° C. $^1$H NMR (250 MHz, CDCl$_3$): δ 8.80 (bs, 1H); 7.53 (m, 1H); 7.35–7.25 (m, 4H); 7.20 (m, 1H); 7.10 (d, J=10.2 Hz, 1H); 6.75 (m, 2H); 1.37 (3, 9H). $^{13}$C NMR (100 MHz, CDCl$_3$): δ 176.8, 155.2, 146.8, 137.5, 136.8, 136.2, 130.0, 128.6, 127.7, 127.3, 127.2, 123.7, 110.8, 35.1, 30.5. Anal. Calcd for C$_{17}$H$_{19}$NO: C, 80.59; H, 7.56; N, 5.53. Found: C, 80.34; H, 7.52; N, 5.51.

EXAMPLE 4

General procedure A was used to convert 2-t-butyl-6-methylaniline (196 mg, 1.2 mmol) to the desired product in 15.5 h. Purification via flash column chromatography (eluants 2:1 hexane:ether) afforded 97 mg (36% yield) of an orange solid. Mp: 115–117° C. $^1$H NMR (200 MHz, CDCl$_3$): δ 8.69 (bs, 1H); 7.41–7.18 (m, 5H); 7.09 (t, J=10.2 Hz, 1H); 6.73 (m, 1H); 6.17 (d, J=10.2 Hz, 1H); 2.06 (s, 3H); 1.32 (s, 9H). $^{23}$C NMR (100 MHz, CDCl$_3$): δ 176.7, 155.2, 148.4, 137.6, 135.1, 130.0, 129.5, 127.9, 125.4, 123.6, 111.0, 35.5, 31.1, 18.6. Anal. Calcd for C$_{18}$H$_{21}$NO: C, 80.86; H, 7.92; N, 5.24. Found: C, 80.61; H, 7.93; N, 5.14.

EXAMPLE 5

General procedure B was used to convert 2,6-dichloroaniline (194 mg, 1.2 mmol) to the desired product in 14.5 h. Purification via flash column chromatography (eluants 2:1 hexane:ether) afforded 200 mg (75% yield) of an orange solid. Mp: 63–65° C. $^1$H NMR (200 MHz, CDCl$_2$): δ 8.48 (bs, 1H); 7.47 (d, J=8.0 Hz, 2H); 7.37 (m, 2H); 7.26 (t, J=8.0 Hz, 1H); 7.13 (t, J=10.2 Hz, 1H); 6.83 (m, 1H); 6.29 (d, J=10.2 Hz, 1H). $^{13}$C NMR (100 MHz, CDCl$_3$): δ 177.1, 152.4, 137.5, 135.7, 134.0, 133.5, 131.7, 129.0, 128.7, 125.3, 111.3. Anal. Calcd for C$_{13}$H$_9$NOCl$_2$: C, 58.67; H, 3.41; N, 5.26. Found: C, 58.78; H, 3.46; N, 5.22.

EXAMPLE 6

General procedure B on half the scale with the modification of 12 mg (0.0125 mmol) Pd$_2$dba$_3$ and 16 mg (0.025 mmol) rac-BINAP was used to convert 2,6-dibromoaniline (151 mg, 0.60 mmol) to the desired product in 15 h. Purification via flash column chromatography (eluants 2:1 hexane:ether) afforded 122 mg (69% yield) of an orange solid. Mp: 73–75° C. $^1$H NMR (200 MHz, CDCl$_3$): δ 8.49 (bs, 1H); 7.68 (d, J=8.0 Hz, 2H); 7.35 (m, 2H); 7.12 (m, 2H); 6.83 (m, 1H); 6.27 (d, J=10.2 Hz, 1H). $^{13}$C NMR (100 MHz, CDCl$_3$): δ 177.1, 152.5, 137.6, 136.3, 135.4, 133.0, 131.9, 129.9, 125.3, 124.4, 111.3. Anal. Calcd for C$_{13}$H$_9$NOBr$_2$: C, 43.98; H, 2.56; N, 3.95. Found: C, 43.88; H, 2.61; N, 3.88.

EXAMPLE 7

General procedure B was used to convert 2,3,4,5,6-pentafluoroaniline (220 mg, 1.2 mmol) to the desired product in 15.5 h. Purification via flash column chromatography (eluants 2:1 hexane:ether) afforded 256 mg (84% yield) of a green solid. The compound was isolated as a hydrate. Mp: 156–158° C. $^1$H NMR (400 MHz, CDCl$_3$): δ 8.19 (bs, 1H); 7.38 (dd, J=8.2, 11.8 Hz, 1H); 7.32 (d, J=11.0 Hz, 1H); 7.15 (t, J=10.2 Hz, 1H); 6.87 (t, J=9.0 Hz, 1H); 6.49 (dt, J=2.6, 10.0 Hz, 1H); 2.14 (s, 2H, coordinated H$_2$O). $^{13}$C NMR (100 MHz, CDCl$_3$): δ 177.2, 151.6, 143.0 (dm, J=250 Hz), 139.7 (dm, J=253 Hz), 138.1 (dm, J=253 Hz), 137.7, 135.2, 132.5, 126.4, 113.7 (dt, J=3.8, 14.2 Hz), 111.6. $^{19}$F NMR (376 MHz, CDCl$_3$): δ −144.5 (m), −157.31 (m), −161.87 (m). Anal. Calcd for C$_{13}$H$_6$NOF$_5$: C, 54.36; H, 2.11; N, 4.88. Found: C, 54.31; H, 2.18; N, 4.81.

EXAMPLE 8

General procedure A was used to convert 3,5-bistrifluoromethylaniline (188 µl, 1.2 mmol) to the desired product in 15.5 h. Purification via flash column chromatography (eluants 2:1 hexane:ether) afforded 313 mg (89% yield) of a green solid. Compound was isolated as a hydrate. $^1$H NMR (400 MHz, CDCl$_3$): δ 8.87 (bs, 1H); 7.75 (s, 2H); 7.66 (s, 1H); 7.38 (dd, J=8.5, 11.8 Hz, 1H); 7.31 (d, J=11.8 Hz, 1H); 7.20 (m, 2H); 6.89 (m, 1H); 2.15 (s, 2.7H, coordinated H$_2$O). 13C NMR (100 MHz, CDCl$_3$): δ 117.5, 151.7, 140.8, 137.8, 135.4, 132.9 (q, J=33.5 Hz), 132.3, 126.6, 122.9 (q, J=271 Hz), 122.7, (d, J=2.9 Hz), 117.9 (t, J=3.4 Hz), 111.1. $^{19}$F NMR (376 MHz, CDCl$_3$): δ −63.6 (s).

EXAMPLE 9

General procedure B was used to convert 2,6-diphenylaniline (294 mg, 1.2 mmol) to the desired product in 16.5 h. Purification via flash column chromatography (eluants 2:1 hexane:ether) afforded 127 mg (37% yield) of a yellow solid.

EXAMPLE 10

General procedure A was used to convert 2,6-difluoroaniline (129 µl, 1.2 mmol) to the desired product in 19 hours. Purification via flash column chromatography (eluants 2:1 hexane:ether) afforded 219 mg (94% yield) of a yellow solid. $^1$H NMR (400 MHz, CDCl$_3$): δ 8.30 (bs, 1H) 7.35 (m, 2H); 7.25 (m, 1H); 7.16 (t, J=10.2 Hz, 1H); 7.05 (m, 2H); 6.84 (m, 1H); 6.55 (dt, J=2.5, 10.2 Hz, 1H). $^{13}$C NMR (100 MHz, CDCl$_3$): δ 177.0, 159.0 (d, J=4.6 Hz), 156.5 (d, J=4.6 Hz), 137.3, 135.5, 131.6, 127.3 (t, J=9.6 Hz), 125.2, 115.5 (t, J=15.6 Hz), 112.1 (m), 111.4. $^{19}$F NMR (376 MHz, CDCl$_3$): δ −116.6 (s). Anal. calcd for C$_{13}$H$_9$NOF$_2$: C, 66.93; H, 3.89; N, 6.01. Found: C, 66.66; H, 3.90; N, 5.97.

EXAMPLE 11

General procedure A was used to convert 2-methyl-6-trifluoromethylaniline (630 µl, 3.6 mmol) to the desired product in 14.5 hours. Purification via flash column chromatography (eluants 2:1 hexane:ether) afforded 781 mg (93% yield). $^1$H NMR (400 MHz, CDCl$_3$): δ 8.50 (bs, 1H); 7.64 (d, J=7.8 Hz, 1H); 7.55 (d, J=7.6 Hz, 1H); 7.41 (at, J=7.8 Hz, 1H); 7.33 (m, 2H); 7.07 (at, J=10.2 Hz, 1H); 6.77 (m, 1H); 6.14 (d, J=10.1 Hz, 1H); 2.17 (s, 3H). $^{13}$C NMR (100 MHz, CDCl$_3$): δ 176.8, 154.2, 138.6, 137.4, 135.8, 134.9, 134.5, 131.1, 128.4 (q, J=29.6 Hz), 127.6, 124.8 (q, J=5.2 Hz), 124.4, 123.3 (q, J=272 Hz), 110.5, 17.7. $^{31}$P NMR (377 MHz, C$_6$D$_6$): δ −62.2. Anal. calcd for C$_{15}$H$_{12}$NOF$_3$: C, 64.51; H, 4.33; N, 5.02. Found: C, 64.23; H, 4.24; N, 4.87.

EXAMPLE 12

General procedure A was used to convert 2-methylaniline (384 µL, 3.6 mmol) to the desired product in 14.5 hours. Purification via flash column chromatography (eluants 2:1 hexane:ether) afforded 561 mg (89% yield). $^1$H NMR (400 MHz, CDCl$_3$): δ 8.57 (bs, 1H); 7.40–7.30 (m, 3H); 7.30–7.21 (m, 3H); 7.12 (dd, J=10, 10.4 Hz, 1H); 6.77 (m, 1H); 6.71 (d, J=10.4 Hz, 1H); 2.21 (s, 3H). $^{13}$C NMR (100 MHz, CDCl$_3$): δ 176.5, 154.5, 137.5, 136.5, 136.2, 134.6, 131.4, 130.2, 127.1, 126.1, 124.2, 110.6, 17.8. Anal. calcd for C$_{14}$H$_{13}$NO: C, 79.59; H, 6.20; N, 6.63. Found: C, 79.62; H, 6.17; N, 6.62.

EXAMPLES 13–22

General Procedure for the Synthesis of Na Salts of 2-Anilinotropones:

To a side arm flask in a glovebox was added NaH (1.2 equiv). The flask was removed from the glovebox and placed on a vacuum line under argon. THF (5–10 mL) was added to the flask, and the flask was cooled with an ice water bath. Slow addition of the 2-anilinotropone (1 equiv) as a solution in THF (3 mL) resulted in vigorous bubbling. When bubbling ceased, the flask was removed from the ice water bath and allowed to warm to rt. After 2 h, the solution was cannula filtered away from the remaining NaH, and the residual NaH was washed with THF (3 mL). The THF was removed in vacuo to produce essentially a quantitative yield of the desired salt as its THF adduct. The amount of THF incorporated varied with different salts and was determined by $^1$H NMR.

EXAMPLE 13

Na Salt of 2-(2,6-diisopropylanilino)tropone: The general procedure was employed with 1.28 g (4.5 mmol) anilinotropone and 120 mg (5 mmol) NaH. The salt was isolated with 1 equiv of THF. $^1$H NMR (250 MHz, C$_6$D$_6$) δ 7.18–7.04 (m, 3H); 6.6–6.4 (m, 3H); 6.32 (dd, J=8.0, 12.2 Hz, 1H); 6.02 (dt, J=3.2, 7.8 Hz, 1H); 3.36 (THF); 2.94 (m, 2H); 1.26 (THF); 1.14 (d, J=7.0 Hz, 6H); 1.00 (d, J=7 Hz, 1H). $^{13}$C NMR (100 MHz, C$_6$D$_6$): δ 177.6, 165.8, 148.7, 139.0, 134.4, 133.5, 124.2, 123.5, 121.2, 118.4, 117.9, 68.0, 28.2, 25.6, 24.9, 23.9.

EXAMPLE 14

Na Salt of 2-(2,6-dimethylanilino)tropone: The general procedure was employed with 405 mg (1.8 mmol) anilinotropone and 50 mg (2 mmol) NaH. The salt was isolated with 2.18 equiv of THF. $^1$H NMR (400 MHz, C$_6$D$_6$): δ 7.05 (m, 2H); 6.92 (m, 1H); 6.58–6.33 (m, 4H); 6.05 (m, 1H); 3.40 (THF); 1.94 (s, 6H); 1.31 (THF).

EXAMPLE 15

Na Salt of 2-(2-t-butylanilino)tropone: The general procedure was employed with 462 mg (1.8 mmol) anilinotropone and 50 mg (5 mmol) NaH. The salt was isolated with 1.5 equiv of THF. $^1$H NMR (250 MHz, C$_6$D$_6$): δ 7.42 (d, J=8.0 Hz, 1H); 6.98 (m, 1H); 6.66 (m, 2H); 6.45 (m, 3H); 6.04 (at, J=9.0 Hz, 1H); 3.44 (THF); 1.37 (THF); 1.29 (s, 9H).

EXAMPLE 16

Na Salt of 2-(2-t-butyl-6-methylanilino)tropone: The general procedure was employed with 303 mg (1.14 mmol) anilinotropone and 31 mg (1.3 mmol) NaH. The salt was isolated with 1.16 equiv of THF. $^1$H NMR (400 MHz, C$_6$D$_6$): δ 7.33 (d, J=7.6 Hz, 1H); 7.07 (d, J=7.6 Hz, 1H); 6.94 (at, J=7.6 Hz, 1H); 6.52 (m, 2H); 6.39 (m, 2H); 6.04 (m, 1H); 3.40 (THF); 1.97 (s, 3H); 1.30 (s, 9H+THF).

EXAMPLE 17

Na Salt of 2-(2,6-diphenylanilino)tropone: The general procedure was employed with 352 mg (1.0 mmol) anilinotropone and 28 mg (1.2 mmol) NaH. The salt was isolated with 0.55 equiv of THF. $^1$H NMR (400 MHz, C$_6$D$_6$): δ 7.28 (d, J=7.6 Hz, 2H); 7.19 (d, J=6.8 Hz, 2H); 7.04 (t, J=7.6 Hz, 1H); 6.81 (m, 6H); 6.63 (d, J=11.6 Hz, 1H); 6.44 (m, 2H); 6.08 (at, J=9.0 Hz, 1H); 6.00 (d, J=10.4 Hz, 1H); 3.52 (THF); 1.39 (THF).

EXAMPLE 18

Na Salt of 2-(2-methyl-6-trifluoromethylanilino)tropone: The general procedure was employed with 688 mg (2.5 mmol) anilinotropone and 71 mg (2.95 mmol) NaH. The salt was isolated with 1 equiv of THF. $^1$H NMR (400 MHz, C$_6$D$_6$): δ 7.39 (d, J=7.6 Hz, 1H); 7.06 (d, J=7.6 Hz, 1H); 6.70 (at, J=7.6 Hz, 1H); 6.57 (m, 2H); 6.45 (dd, J=8.2, 11.6 Hz, 1H); 6.28 (d, J=11.6 Hz, 1H); 6.08 (at, J=8.8 Hz, 1H); 3.46 (THF); 1.88(s, 3H); 1.33 (THF).

EXAMPLE 19

Na Salt of 2-(2,6-dichloroanilino)tropone: The general procedure was employed with 658 mg (2.5 mmol) anilinotropone and 71 mg (2.95 mmol) NaH. The salt was isolated with 1.6 equiv of THF. $^1$H NMR (400 MHz, C$_6$D$_6$): δ 7.08 (d, J=8.0 Hz, 2H); 6.73 (d, J=10.4 Hz, 1H); 6.59 (at, J=10.2 Hz, 1H); 6.51 (m, 1H); 6.39 (m, 2H); 6.11 (at, J=9.2 Hz, 1H); 3.50 (THF); 1.35 (THF).

EXAMPLE 20

Na Salt of 2-(2,6-dibromoanilino)tropone: The general procedure was employed with 721 mg (2.0 mmol) anilinotropone and 58 mg (2.44 mmol) NaH. The salt was isolated with 1 equiv of THF. $^1$H NMR (400 MHz, C$_6$D$_6$): δ 7.26 (m, 2H); 6.74 (m, 1H); 6.61 (m, 1H); 6.50 (m, 1H); 6.35 (d, J=11.2 Hz, 1H); 6.23 (m, 1H); 6.14 (m, 1H); 3.51 (THF); 1.33 (THF).

EXAMPLE 21

Na Salt of 2-(2-methylanilino)tropone: The general procedure was employed with 508 mg (2.4 mmol) anilinotropone and 69 mg (2.9 mmol) NaH. The salt was isolated with 0.89 equiv of THF. $^1$H NMR (400 MHz, C$_6$D$_6$): δ 7.11 (m, 2H); 6.93 (m, 1H); 6.64–6.45 (m, 4H); 6.41 (dd, J=8.6, 11.4 Hz, 1H); 6.08 (at, J=9.0 Hz, 1H); 3.46 (THF); 1.89 (s, 3H); 1.32 (THF).

EXAMPLE 22

Na Salt of 2-(2,3,4,5,6-pentafluoroanilino)tropone: The general procedure was employed with 581 mg (1.9 mmol) anilinotropone and 100 mg (4.2 mmol) NaH. The salt was isolated with no excess THF. $^1$H NMR (400 MHz, d$_6$-acetone): δ 6.85 (at, H=10.2 Hz, 1H); 6.73 (d, J=10 Hz, 1H); 6.69 (at J=11.4 Hz, 1H); 6.19 (d, J=11.2 Hz, 1H); 6.14 (at, J=9.2 Hz, 1H).

EXAMPLES 23–32

General Procedure for the Synthesis of Ni Complexes:

To a flame dried Schlenk flask in a glovebox were added the sodium salt of a 2-anilinotropone·THF (1 equiv) and (Ph$_3$P)$_2$Ni(Ph)(Cl) (1 equiv). The flask was removed from the glovebox, was placed on a vacuum line under Ar, and was cooled to −30° C. with a dry ice/acetone bath. THF (~15 mL) was added to the flask, which was allowed to warm to RT over 1 h. The reaction was allowed to stir at ambient temperature for 1 h. THF was removed in vacuo and the crude reaction mixture dissolved in toluene (~15 mL). Cannula transfer onto a pad of Celite was followed by filtration under Ar. The Celite® pad was washed with toluene (3×5 mL), and the solvent volume was reduced to 3–5 mL. Pentane (50 mL) was added, and the Schlenk flask was placed in a −30° C. freezer overnight. Solvent was removed from the precipitate via cannula filtration, and the residual solid was washed with pentane (3×10 mL). Drying in vacuo produces the desired nickel complex.

EXAMPLE 23

2-(2,6-Diisopropylanilino)tropone Ni Complex (VIII): The general procedure was employed with 201 mg (0.54 mmol) of the sodium salt and 372 mg (0.54 mmol) of (Ph$_3$P)$_2$Ni(Ph)(Cl) to afford 241 mg (67%) of the desired complex as a yellow-orange solid. $^1$H NMR (400 MHz, C$_6$D$_6$): δ 7.63 (m, 6H); 7.08 (d, J=7.0 Hz, 2H); 6.98 (m, 12H); 6.76 (d, J=10.4 Hz, 1H); 6.58 (at, J=9.9 Hz, 1H). 6.53 (d, J=11.5 Hz, 1H); 6.45–6.33 (m, 4H); 6.13 (at, J=9.4 Hz, 1H); 3.82 (sept, J=6.8 Hz, 2H); 1.32 (d, J=6.8 Hz, 6H); 1.09 (d, J=6.8 Hz, 6H). $^{13}$C NMR (100 MHz, C$_6$D$_6$): δ 180.2 (d, J=7.6 Hz), 169.6 148.9 (d, J=45 Hz), 144.4, 142.3, 138.1 (d, J=2.2 Hz), 134.6 (d, J=10.5 Hz), 133.1, 132.0, 131.6, 129.9 (d, J=1.9 Hz), 125.9, 125.5 (d, J=2 Hz), 123.7, 122.2, 121.7, 121.3, 121.1, 29.0, 25.9, 23.9. $^{31}$P NMR (162 MHz, C$_6$D$_6$): δ 28.9. Anal. calcd for C$_{43}$H$_{42}$NOPNi: C, 76.12; H, 6.24; N, 2.06. Found: C, 75.83; H, 6.24; N, 1.98.

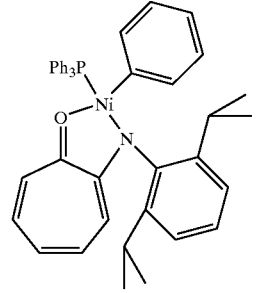

(VIII)

EXAMPLE 24

2-(2,6-dimethylanilino)tropone Ni Complex: The general procedure was employed with 172 mg (0.54 mmol) of the sodium salt and 372 mg (0.54 mmol) of (Ph$_3$P)$_2$Ni(Ph)(Cl) to afford 190 mg (57%) of the desired complex as a yellow-orange solid. $^1$H NMR (400 MHz, CD$_2$Cl$_2$): δ 7.54 (m, 6H); 7.39 (m, 3H); 7.28 (m, 6H); 7.21 (d, J=8 Hz, 2H); 7.09 (dd, J=10, 10.6 Hz, 1H); 6.99 (m, 2H); 6.94 (d, J=10.6 Hz, 1H); 6.71 (d, J=10.7 Hz, 1H); 6.63 (at, J=9.5 Hz, 1H); 6.56 (t, J=8 Hz, 1H); 6.22 (m, 2H); 6.14 (m, 2H); 2.21 (s, 6H). $^{13}$C NMR (100 MHz, CD$_2$Cl$_2$): δ 179.9 (d, J=7.2 Hz), 167.7, 150.3 (d, J=44.5 Hz), 146.4, 136.9 (d, J=1.8 Hz), 134.7, 134.6 (d, J=10.7 Hz), 134.3, 131.8 (d, J=1.9 Hz), 131.4, 130.1, 128.2 (d, J=9.7 Hz), 127.7, 124.8 (d, J=2.6 Hz), 124.3, 122.0, 121.1, 120.5, 117.7, 18.3. $^{31}$P NMR (162 MHz, C$_6$D$_6$): δ 29.03. Anal. calcd for C$_{39}$H$_{34}$NOPNi: C, 75.26; H, 5.51; N, 2.25. Found: C, 75.49; H, 5.57; N, 2.38.

EXAMPLE 25

2-(2-t-Butylanilino)tropone Ni Complex: The general procedure was employed with 201 mg (0.53 mmol) of the sodium salt and 372 mg (0.54 mmol) of (Ph$_3$P)$_2$Ni(Ph)(Cl) to afford 195 mg (57%) of the desired complex as a yellow-orange solid. $^1$H NMR (400 MHz, CD$_2$Cl$_2$): δ 7.47 (m, 6H); 7.38 (m, 3H); 7.28 (m, 6H); 7.18 (dd, J=1.4, 8 Hz, 1H); 7.11 (bs, 1H); 6.95 (at, J=10.2 Hz, 1H); 6.81 (m, 2H); 6.72 (m, 1H); 6.55 (M, 2H); 6.46 (d, J=9.4 Hz, 1H); 6.42 (dd, J=1.6, 7.7 Hz, 1H); 6.23 (m, 2H); 6.07 (bs, 1H); 1.51 (s, 9H). $^{13}$C NMR (100 MHz, CD$_2$Cl$_2$): δ 179.9 (d, J=7.5 Hz), 169.1, 151.3 (d J=45 Hz), 146.9, 142.3, 138.4 (broad), 137.8 (broad), 134.8, 134.6 (d, J=10.5 Hz), 133.7, 131.9, 131.5, 130.1 (d, J=1.9 Hz), 128.9, 128.8, 128.2 (d, J=9.7 Hz), 126.3, 125.1 (broad), 124.2, 121.6, 120.9, 120.7, 120.5, 36.4, 32.8. $^{31}$P NMR (162 MHz, CD$_2$Cl$_2$): δ 29.34. Anal. calcd for C$_{41}$H$_{38}$NOPNi: C, 75.71; H, 5.89; N, 2.15. Found: C, 75.76; H, 5.92; N, 2.19.

EXAMPLE 26

2-(2-t-Butyl-6-methylanilino)tropone Ni Complex: The general procedure was employed with 219 mg (0.59 mmol) of the sodium salt and 409 mg (0.59 mmol) of (Ph$_3$P)$_2$Ni(Ph)(Cl) to afford 185 mg (47%) of the desired complex as a yellow-orange solid. $^1$H NMR (400 MHz, C$_6$D$_6$): δ 7.63 (m, 6H); 7.23 (bs, 1H); 7.15 (m, 1H); 6.98 (m, 10H); 6.81 (m, 2H); 6.75 (d, J=10.4 Hz, 1H); 6.58 (at, J=10 Hz, 1H); 6.48 (m, 2H); 6.41 (m, 3H); 6.11 (at, J=9.0 Hz, 1H); 2.46 (s, 3H); 1.69 (s, 9H). $^{13}$C NMR (100 MHz, CD$_2$Cl$_2$): δ 179.8 (d, J=7.3 Hz), 168.1, 149.3 (d, J=45.3 Hz), 145.6, 142.1, 138.3 (broad), 137.2 (broad), 134.7, 134.5 (d, J=10.5 Hz), 133.9, 133.1, 131.9, 131.4, 130.1, 128.2 (d, J=9.9 Hz), 128.1, 127.1, 124.9 (broad), 124.4, 121.7, 121.1, 120.4, 119.7, 36.9, 33.3, 19.6. $^{31}$P NMR (162 MHz, CD$_2$Cl$_2$): δ 29.02. Anal. calcd for C$_{42}$H$_{40}$NOPNi: C, 75.92; H, 6.07; N, 2.11. Found: C, 75.75; H, 6.11; N, 2.15.

EXAMPLE 27

2-(2,6-Diphenylanilino)tropone Ni Complex: The general procedure was employed with 225 mg (0.55 mmol) of the sodium salt and 380 mg (0.55 mmol) of (Ph$_3$P)$_2$Ni(Ph)(Cl) to afford 220 mg (54%) of the desired complex as a yellow-orange solid. Compound was isolated with 0.33 eq of toluene. $^1$H NMR (400 MHz, C$_6$D$_6$): δ 7.95 (d, J=7.6 Hz, 4H); 7.49 (m, 6H); 7.20 (m, 6H); 7.13 (m, 6H); 6.98 (8H+toluene); 6.77 (d, J=11.6 Hz, 1H); 6.55 (m, 2H); 6.4 (m, 4H); 6.02 (m, 1H); 2.09 (toluene). $^{13}$C NMR (100 MHz, CD$_2$Cl$_2$): δ 179.6 (d, J=7.5 Hz), 168.9, 148.0 (d, J=45.1 Hz), 144.6, 140.8, 138.3 (d, J=2.7 Hz), 137.0, 134.8, 134.5 (d, J=10.6 Hz), 133.8, 131.8, 131.3, 130.5, 130.2, 130.0 (d, J=1.9 Hz), 129.3, 128.5, 128.1 (d, J=9.8 Hz), 127.7, 127.0, 125.6, 125.2, 124.9 (d, 1.9 Hz), 122.0, 121.2, 121.1, 120.5, 21.5. $^{31}$P NMR (162 MHz, C$_6$D$_6$): δ 29.03. Anal. calcd for C$_{49}$H$_{38}$NOPNi·0.33 toluene : C, 79.3; H, 5.27; N, 1.80. Found: C, 79.24; H, 5.37; N, 1.77.

EXAMPLE 28

2-(2-Methyl-6-trifluoromethylanilino)tropone Ni Complex: The general procedure was employed with 192 mg (0.51 mmol) of the sodium salt and 357 mg (0.51 mmol) of (Ph$_3$P)$_2$Ni(Ph)(Cl) to afford 205 mg (59%) of the desired complex as a yellow-orange solid. $^1$H NMR (400 MHz, CD$_2$Cl$_2$): δ 7.49 (m, 6H); 7.37 (m, 3H); 7.27 (m, 7H); 7.04 (d, J=9.9 Hz, 1H); 6.96 (m, 2H); 6.86 (m, 2H); 6.63 (d, J=10.6 Hz, 1H); 6.55 (m, 2H); 6.17 (m, 3H); 6.05 (m, 1H); 2.17 (s, 3H). $^{13}$C NMR (100 MHz, CD$_2$Cl$_2$): spectrum is difficult to interpret due to extensive F coupling; δ 180.1 (d, J=7.3 Hz), 168.0, 149.4 (d, J=46.0 Hz), 146.4, 138.1, 136.8, 135.2, 134.8, 134.6 (d, J=10.6 Hz), 134.4, 134.0, 131.8, 131.3, 130.1 (d J=2.5 Hz), 128.2 (d, J=9.7 Hz), 126.2, 125.1 (broad), 124.8, 124.7 (broad), 124.5 (q, J=5.6 Hz), 124.3, 123.5, 122.4, 121.9, 121.1, 118.9, 18.2. $^{31}$P NMR (162 MHz, CD$_2$Cl$_2$): δ 29.37. Anal. calcd for: C, 69.25; H, 4.62; N, 2.07. Found C$_{39}$H$_{31}$NOPNiF$_3$: C, 69.15; H, 4.57; N, 2.10.

EXAMPLE 29

2-(2,6-Dichloroanilino)tropone Ni Complex: The general procedure was employed with 200 mg (0.50 mmol) of the sodium salt and 344 mg (0.50 mmol) of (Ph$_3$P)$_2$Ni(Ph)(Cl) to afford 250 mg (75%) of the desired complex as a yellow-orange solid. $^1$H NMR (400 MHz, C$_6$D$_6$): δ 7.54 (m, 6H); 7.39 (m, 3H); 7.29 (m, 6H); 7.09 (dt, J=1.0, 10.2 Hz, 1H); 6.96 (m, 5H); 6.72 (d, J=10.8 Hz, 1H); 6.70 (d, J=8.1 Hz, 1H); 6.63 (at, J=9.5 Hz, 1H); 6.23 (at, J=9.5 Hz, 1H) 6.23 (m, 2H); 6.14 (m, 2H). $^{13}$C NMR (100 MHz, CD$_2$Cl$_2$): δ 180.2 (d, J=6.8 Hz), 167.7, 149.9 (d, J=45.3 Hz), 144.2, 137.1 (d, J=1.7 Hz), 135.5, 134.8, 134.7 (d, J=10.6 Hz), 131.7, 131.3, 130.2 (d, J=2 Hz), 128.2 (d, J=9.7 Hz), 128.1, 125.6, 124.9 (d, J=2.1 Hz), 123.2, 122.9, 121.4, 117.8. $^{31}$P NMR (162 MHz, CD$_2$Cl$_2$): δ 29.13. Anal. calcd for C$_{37}$H$_{28}$NOPNiCl$_2$: C, 67.00; H, 4.26; N, 2.11. Found: C, 66.95; H, 4.37; N, 2.15.

EXAMPLE 30

2-(2,6-Dibromoanilino)tropone Ni Complex: The general procedure was employed with 220 mg (0.49 mmol) of the sodium salt and 341 mg (0.49 mmol) of (Ph$_3$P)$_2$Ni(Ph)(Cl) to afford 315 mg (85%) of the desired complex as a yellow-orange solid. $^1$H NMR (400 MHz, CD$_2$Cl$_2$): δ 7.54 (m, 6H); 7.39 (m, 3H); 7.28 (m, 6H); 7.21 (d, J=8.0 Hz, 2H); 7.09 (m, 1H); 7.00 (m, 2H); 6.94 (d, J=10.4 Hz, 1H); 6.72 (d, J=10.8 Hz, 1H); 6.63 (at, J=9.4 Hz, 1H); 6.56 (t, J=8.0 Hz, 1H); 6.22 (m, 2H); 6.14 (t, J=7.2 Hz, 2H). $^{13}$C NMR (100 MHz, CD$_2$Cl$_2$): δ 180.2 (d, J=6.8 Hz), 167.3, 149.6 (d, J=45.7 Hz), 146.5, 137.4, 135.5, 134.8, 134.7 (d, J=10.6 Hz), 132.0, 131.7, 131.3, 130.2 (d, J=1.6 Hz), 128.2 (d, J=9.8 Hz), 126.4, 124.9 (d, J=2 Hz), 123.2, 123.0, 122.3, 121.4, 118.0. $^{31}$P NMR (162 MHz, CD$_2$Cl$_2$): δ 29.03. Anal. calcd for C$_{37}$H$_{28}$NOPNiBr$_2$: C, 59.08; H, 3.75; N, 1.86. Found: C, 59.35; H, 3.82; N, 1.90.

EXAMPLE 31

2-(2-Methylanilino)tropone Ni Complex: The general procedure was employed with 100 mg (0.34 mmol) of the sodium salt and 234 mg (0.34 mmol) of (Ph$_3$P)$_2$Ni(Ph)(Cl) to afford 105 mg (51%) of the desired complex as a yellow-orange solid. $^1$H NMR (400 MHz, CD$_2$Cl$_2$): δ 7.50 (m, 6H); 7.39 (m, 3H); 7.28 (m, 6H); 6.98 (dt, J=1.0, 10.2 Hz, 1H); 6.87 –6.67 (m, 6H); 6.59 (d, J=10.4 Hz, 1H); 6.53 (dd, J=1.3, 7.6 Hz, 1H); 6.49 (at, J=9.5 Hz, 1H); 6.27 (d, J=11.6 Hz, 1H); 6.18 (m, 2H); 6.06 (bs, 1H); 2.19 (s, 3H). $^{13}$C NMR (100 MHz, CD$_2$Cl$_2$): δ 179.9 (d, J=7.5 Hz), 168.5, 151.6 (d, J=44.4 Hz), 147.8, 138.0 (broad), 137.1 (broad), 134.7, 134.6 (d, J=10.6 Hz), 134.1, 132.1, 131.9, 131.5, 130.1 (d, J=2.3 Hz), 130.0, 128.2 (d, J=9.7 Hz), 126.3, 126.2, 125.0 (broad), 124.2, 122.0, 121.0, 120.8, 118.6, 17.9. $^{31}$P NMR (162 MHz, CD$_2$Cl$_2$): δ 29.43. Anal. calcd for C$_{38}$H$_{32}$NOPNi: C, 75.02; H, 5.30; N, 2.30. Found: C, 74.12; H, 5.33; N, 2.31.

EXAMPLE 32

2-(2,3,4,5,6-Pentafluoroanilino)tropone Ni Complex: The general procedure was employed with 136 mg (0.44 mmol)

of the sodium salt and 308 mg (0.44 mmol) of $(Ph_3P)_2Ni(Ph)(Cl)$ to afford 169 mg (57%) of the desired complex as a yellow-orange solid. $^1H$ NMR (400 MHz, $CD_2Cl_2$): δ 7.52 (m, 6H) 7.39 (m, 3H); 7.30 (m, 6H); 7.18 (dt, J=0.9, 10.25 Hz, 1H); 7.06 (m, 1H); 6.87 (d, J=7.2 Hz, 2H); 6.80 (d, J=10.8 Hz, 1H); 6.74 (at, J=9.6 Hz, 1H); 6.50 (d, J=11.2 Hz, 1H); 6.36 (t, J=7.15 Hz, 1H); 6.28 (m, 2H). $^{13}C$ NMR (100 MHz, $CD_2Cl_2$): spectrum difficult to interpret due to extensive F coupling. δ 180.8 (d, J=6.5 Hz), 169.1, 152.2 (d, J=45.5 Hz), 136.8, 136.2, 135.4, 134.6 (d, J=10.7 Hz), 132.3 (m), 131.4, 131.0, 130.3 (d, J=1.9 Hz), 128.9 (m), 128.3 (d, J=9.8 Hz), 125.5 (d, J=2.5 Hz), 124.5, 124.3, 122.0, 118.0. $^{31}P$ NMR (162 MHz, $CD_2Cl_2$): δ 29.71. $^{19}F$ NMR (377 MHz, $CD_2Cl_2$): δ −147.73 (m), −163.75 (t, J=22.6 Hz), −166.52 (m). Anal. calcd for $C_{37}H_{25}NOPNiF_5$: C, 64.94; H, 3.68; N, 2.05. Found: C, 64.45; H, 3.90; N, 2.31.

EXAMPLE 33

Bistropone Ni Complex from 2-(2,6-diisopropylanilino)-tropone:

To a flame dried Schlenk flask in a glovebox were added the sodium salt of the 2-anilinotropone·THF (377 mg, 0.90 mmol)) and $(DME)NiBr_2$ (139 mg, 0.45 mmol). The flask was removed form the glovebox and placed on a vacuum line under Ar. $Et_2O$ (20 mL) was added to the flask, and the reaction was allowed to stir at room temperature for 15 h. The crude reaction mixture was filtered through filter paper and condensed to produce 240 mg (88%) of a red-brown solid. $^1H$ NMR (400 MHz, $C_6D_6$): δ 7.29–7.21 (m, 6H); 6.26–6.18 (m, 8H); 5.92 (m, 2H); 4.18 (sept, J=6.8 Hz, 4H); 1.74 (d, J=6.8 Hz, 12H); 1.19 (d, J=6.8 Hz, 12H). $^{13}C$ NMR (100 MHz, $C_6D_6$): δ 180.4, 168.9, 143.6, 141.1, 134.6, 133.8, 126.7, 124.0, 122.8, 120.7, 119.3, 29.2, 24.5, 24.1. Anal. calcd for $C_{38}H_{42}N_2O_2Ni$: C, 73.67; H, 7.16; N, 4.50. Found: C, 74.10; H, 7.25; N, 4.39.

EXAMPLES 34–40

Polymerizations of Ethylene with (VIII)

A 1000 mL Parr® autoclave was heated under vacuum up to 110° C., was cooled, and was backfilled with ethylene. The autoclave was charged with toluene (190 mL), was degassed with ethylene (3×1.38 MPa), and was pressurized with ethylene to 2.76 MPa for the reaction. The stirring motor was engaged, and the reactor was allowed to equilibrate at the desired temperature for 10 min. In a glove box, a Schlenk flask was charged with the catalyst. The Schlenk flask was removed from the glove box and was placed on a vacuum line under Ar. The catalyst was dissolved in toluene (10 mL) and was cannula transferred into the autoclave which had been vented. The autoclave was sealed and was pressurized to 2.76 MPa. At the appropriate time, the reactor was vented, and the polymer was isolated via filtration and was dried in a vacuum oven. Variations in time, temperature, solvent, and catalyst loading were employed to generate the data in Table 2.

EXAMPLES 41–80

Unless otherwise noted, the "catalyst" (Ni compound) was (VIII).

General Procedure for High Pressure (Above Atmospheric) Ethylene Polymerizations.

A 1000 mL Parr autoclave was heated under vacuum up to 110° C. and then was cooled to the desired reaction temperature and backfilled with ethylene. The autoclave was charged with solvent (190 mL), degassed with ethylene (2×1.38 MPa), and pressurized with ethylene to 1.38 MPa. The stirring motor was engaged, and the reactor allowed to equilibrate at the desired temperature for approximately 10 min. In a glovebox, a side arm flask was charged with the catalyst. The flask was removed from the glovebox and placed on a vacuum line under Ar. The catalyst was dissolved in 10 mL toluene and cannula transferred into the vented autoclave with stirring motor off. The autoclave was sealed and pressurized to the desired level, and the stirring motor was reengaged. After the prescribed reaction time, the stirring motor was stopped, the reactor was vented, and the polymer isolated via precipitation from methanol and dried in a vacuum oven. This procedure was employed with modifications in time, temperature, ethylene pressure, and solvent. For the additive studies, 170 mL of toluene and 20 mL of the respective additive were used in place of the 190 mL toluene mentioned above. For the studies with excess $PPh_3$, both the catalyst and $PPh_3$ were added in the same 10 mL toluene.

Procedure for Ethylene Polymerization at 1 atm.

In a glovebox, a side arm flask was charged with the catalyst (7.6 μmol). The flask was removed from the glovebox and placed on a vacuum line under argon. Toluene (40 mL) was added to flask, and the flask was placed in an 80° C. oil bath. After 10 min, the flask was evacuated and backfilled with ethylene 3 times and left open to ethylene for the duration of the polymerization. After 2 h, the reaction was cooled to RT and poured into 200 mL stirred MeOH. After stirring 12 h, an oil had separated out on the bottom. The solvent was decanted and the residual oil dissolved in hexane. This solution was filtered through a pad of silica gel with additional hexane, and the solvent was removed in vacuo to yield polymer.

Some of these polymerization runs are reported under different example numbers in the tables. They are repeated to illustrate the effect of different variables on the polymerization. Table 3 shows the effect of temperature, Table 4 the effect of ethylene pressure, Table 5 the effect of catalyst loading, Table 6 the effect of various additives, and Table 7 the effect of various solvents. Table 8 shows the effect of varying the substitution on the phenyl ring derived from the aniline and the column labeled "Ar" gives that substitution pattern.

EXAMPLES 81–82

1-Hexene Polymerizations with (VIII)

A Schlenk flask in a glove box was charged with the catalyst. The flask was removed from the glove box and was placed on a vacuum line under Ar. Toluene and 1-hexene were added to a separate flask, and the flask was placed in an oil bath at the appropriate temperature and was allowed to equilibrate for 10 min. The catalyst was dissolved in toluene (0.50 mL) and was cannula transferred into the toluene/1-hexene solution. The solution was allowed to stir for the prescribed time, and the solvent and excess 1-hexene were removed to yield the crude polymer. Further purification was effected via filtration of a hexane solution of the polymer through a pad of Celite® and removal of the solvent in vacuo. These conditions were used to generate the data in Table 9.

TABLE 2

| Ex. | mol cat (× 10⁶) | Solvent | temp (° C.) | time (h) | Yield (g) | TON[a] | $M_n$ | PDI | branches/ 1000 carbons | $T_m$ (° C.) |
| --- | --- | --- | --- | --- | --- | --- | --- | --- | --- | --- |
| 14 | 3.0 | Toluene | 40 | 1.0 | 0.125 | 1490 | 68000 | 3.57 | 14 | 121 |
| 15 | 3.0 | Toluene | 60 | 1.0 | 0.740 | 8800 | 151000 | 2.39 | 29 | 102 |
| 16 | 3.0 | Toluene | 80 | 1.0 | 1.14 | 13600 | 101000 | 1.98 | 48 | 82 |
| 17 | 10.0 | Toluene | 40 | 1.0 | 1.615 | 5770 | 186000 | 3.67 | 10 | 124 |
| 18 | 14.8 | Toluene | 60[b] | 0.5 | 13.66 | 33000 | 57000 | 2.80 | 64 | 87 |
| 19 | 6.0 | CH₂Cl₂ | 40 | 1.0 | 0.312 | 1857 | 86000 | 4.04 | — | 116 |
| 20 | 7.6 | Hexane | 40 | 1.0 | 0.527 | 2480 | 112000 | 3.92 | — | 122 |

[a] mol PE/mol cat
[b] Reaction exotherm to 103° C.

TABLE 3[a]

| Ex. | temp (° C.) | yield (g) | TON[b] | $M_n$ | PDI | Branches per 1000 carbons |
| --- | --- | --- | --- | --- | --- | --- |
| 41 | 40 | 1.20 | 8240 | 203946 | 2.81 | 8 |
| 42 | 60 | 6.78 | 31900 | 292215 | 1.97 | 27 |
| 43 | 80 | 11.41 | 53600 | 118962 | 1.75 | 49 |
| 44 | 100 | 4.04 | 19000 | 60714 | 1.85 | 67 |

[a] 2.76 MPa E pressure, 7.6 μmol catalyst, 1 h
[b] mol PE/mol cat

TABLE 4

| Ex. | ethylene (MPa) | yield (g) | TON[b] | $M_n$ | PDI | Branches per 1000 carbons |
| --- | --- | --- | --- | --- | --- | --- |
| 45[c] | 14 | 0.145 | 980 | 6700 | 2.03 | 113 |
| 46 | 50 | 4.0 | 27000 | 49774 | 1.68 | 90 |
| 47 | 100 | 6.3 | 42500 | 62485 | 1.89 | 76 |
| 48 | 200 | 9.2 | 62120 | 89637 | 1.84 | 61 |
| 49 | 200[d] | 7.63 | 52400 | 91500 | 1.84 | 61 |
| 50 | 400 | 7.1 | 47800 | 103908 | 1.95 | 45 |
| 51 | 600 | 2.6 | 17500 | 119571 | 1.97 | 41 |

[a] 5.2 μmol catalyst, 1 h, 80° C.
[b] kg PE/mol catalyst.
[c] 7.6 μmol cat, 40 mL toluene, 2 h.
[d] 10 min run, TOF 8.8 × 10⁶ g PE · mol cat⁻¹ · h⁻¹.

TABLE 5[a]

| Ex. | mol cat (× 10⁶) | yield (g) | TON[b] | $M_n$ | PDI | Branches per 1000 carbons | $T_m$ (° C.) |
| --- | --- | --- | --- | --- | --- | --- | --- |
| 52 | 3.0 | 0.74 | 8800 | 151000 | 2.39 | 29 | 102 |
| 53 | 7.6 | 6.78 | 31900 | 292215 | 1.97 | 27 | |
| 54[c] | 14.8 | 13.66 | 33000 | 57000 | 2.80 | 64 | 87 |

[a] Ethylene pressure 2.76 MPa, 60° C., 1 h,
[b] mol PE/mol cat
[c] 30 min run, exotherm to 103° C.

TABLE 6

| Ex. | Solvent | additive (mL) | yield (g) | TON[b] | $M_n$ | PDI | Branches per 1000 carbons |
| --- | --- | --- | --- | --- | --- | --- | --- |
| 55 | Toluene | none | 2.82 | 19000 | 189000 | 1.81 | 37 |
| 56 | Toluene | EtOAc (1) | 2.28 | 15700 | 192000 | 1.80 | 36 |
| 57 | Toluene | H₂O (1) | 1.40 | 9600 | 128000 | 1.85 | 38 |
| 58 | Hexane | H₂O (1) | 1.48 | 10200 | 135000 | 1.89 | 39 |
| 59 | Toluene | EtOH (1) | 1.12 | 7700 | 131000 | 1.88 | 37 |
| 60 | Toluene | NEt₃ (1) | 2.74 | 18800 | 146000 | 2.02 | 38 |
| 61 | Toluene | EtOAc (20) | 3.82 | 26200 | 163000 | 1.92 | 43 |
| 62 | Toluene | H₂O (20) | 0.850 | 5800 | 86000 | 2.31 | 41 |
| 63 | Toluene | EtOH (20) | 0.160 | 1100 | 21000 | 2.35 | 48 |
| 64 | Toluene | NEt₃ (20) | 0.720 | 5000 | 87000 | 1.54 | 37 |

[a] 5.3 μmol catalyst, ethylene pressure 1.38 MPa, 10 min, (200-X) mL solvent, X = additive.
[b] mol PE/mol cat

TABLE 7

| Ex. | solvent | yield (g) | TON[b] | $M_n$ | PDI | branches per 1000 carbons |
|---|---|---|---|---|---|---|
| 65 | toluene | 2.82 | 19000 | 189000 | 1.81 | 37 |
| 66 | THF | 3.34 | 22500 | 146000 | 1.81 | 39 |
| 67 | hexane | 2.59 | 17400 | 163000 | 1.79 | 35 |
| 68 | PhCl | 4.78 | 32200 | 182000 | 1.90 | 46 |
| 69 | PhCl[b] | 8.82 | 59300 | 71300 | 2.08 | 67 |
| 70 | EtOAc | 0.340 | 2290 | 66000 | 4.01 | 33 |

[a]Ethylene pressure 1.38 MPa, 60° C., 10 min, 5.3 μmol catalyst.
[b]mol PE/mol cat [b]80° C.

TABLE 8[a]

| Ex. | Ar | Yield (g) | TON[b] | $M_n$ | PDI | Branches per 1000 carbons |
|---|---|---|---|---|---|---|
| 71 | 2,6-di-i-Pr | 7.63 | 52400 | 91500 | 1.84 | 61 |
| 72 | 2,6-diMe | 4.74 | 32600 | 42400 | 1.74 | 61 |
| 73 | 2-CH$_3$-6-CF$_3$ | 6.0 | 41200 | 87900 | 1.94 | 59 |
| 74 | 2,6-diPh | 8.70 | 59800 | 94900 | 1.77 | 53 |
| 75 | 2,6-diCl | 3.40 | 23400 | 10000[c] | 1.96 | 53 |
| 76 | 2,6-diBr | 3.46 | 23800 | 22300 | 1.93 | 56 |
| 77 | 2-t-Bu-6-CH$_3$ | 0.880 | 6000 | 115000 | 2.02 | 73 |
| 78 | 2-t-Bu | Trace | | 17600 | 2.13 | 72 |
| 79 | 2-CH$_3$ | 0.810? | 5600 | 4700[b] | 2.41 | 57 |
| 80 | pentafluoro | 1.02? | 7000 | 1570[b] | 3.03 | 49 |

[a]Ethylene pressure 1.38 MPa, 5.2 μmol catalyst, 80° C., 10 min.
[b]mol PE/mol cat
[c]$M_n$ determined by $^1$H NMR

TABLE 9

| Ex. | mol cat (× 10[6]) | Solvent[a] | 1-Hexene (vol %) | Temp (° C.) | time (h) | yield (mg) | TO | DP | branches/ 1000 carbons |
|---|---|---|---|---|---|---|---|---|---|
| 81 | 7.6 | Toluene | 50 | 40 | 3 | 84 | 130 | 21 | 147 |
| 82 | 7.6 | Toluene | 50 | 60 | 3 | 127 | 200 | 16 | 152 |

[a]Total solution volume 2 mL

Example 83
Synthesis of (IX)

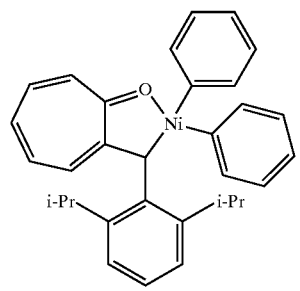

(IX)

Example 84
Synthesis of (X)

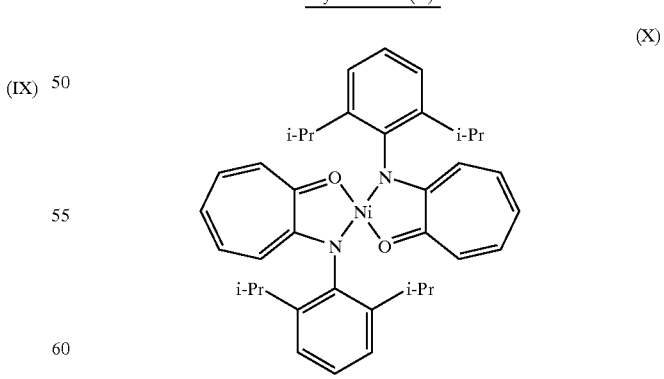

(X)

To separate flame dried Schlenk flasks in a glove box were added the sodium salt of 2-(2,6-di-i-propylanilino) tropone·THF made in Example 12 (375 mg, 1.0 mmol), and (TMEDA)Ni(Ph)(Cl) [see E. Wenschub, *Z. Chem.*, vol. 27, p. 448 (1987)] (286 mg, 1.0 mmol). Both flasks were removed from the glove box and placed on a vacuum line under Ar. Toluene (10 mL) was added to each flask, and the flask containing (TMEDA)Ni(Ph)(Cl) was cooled to −40° C. (acetone/dry ice bath). The toluene solution of the ligand salt was slowly cannula transferred into the precooled flask (10 min). After complete transfer (washed with 5 mL toluene), the reaction was maintained at −40° C. for 2 h and then allowed to warm to RT over one h. The reaction mixture was cannula transferred onto a pad of Celite® and filtered under Ar. The Celite pad was washed with toluene (2×10 mL), and the solvent volume was reduced in vacuo to 10 mL. Pentane (50 mL) was added, and the Schlenk flask was placed in a −30° C. freezer overnight. Solvent was removed from the precipitate via cannula filtration, and the residual solid was washed with pentane (3×5 mL). Drying in vacuo produced 150 mg (30%) of an orange solid. $^1$H NMR (400 MHz, C$_6$D$_6$): δ 8.52 (dd, J=6.6, 1.6 Hz, 2H); 7.32 (dd, J=8.0, 1.2 Hz, 2H); 7.07 (m, 4H); 6.76 (t, J=7.2 Hz, 2H); 6.67 (m, 2H); 6.47 (tt, J=7.6, 1.6 Hz, 1H); 6.37 (d, J=11.5 Hz, 1H); 6.27 (ddd, J=11.6, 8.8, 1.2 Hz, 1H); 6.13 (t, J=9.4 Hz, 1H); 6.07 (m, 2H); 3.29 (sept, J=6.8 Hz, 2H); 1.39 (d, J=6.8 Hz, 6H); 1.10 (d, J=6.8 Hz, 6H). $^{13}$C NMR (100 MHz, C$_6$D$_6$): δ 179.8, 170.5, 152.6, 152.2, 144.6, 142.7, 137.1, 136.0, 134.8, 132.8, 126.3, 125.1, 123.9, 123.3, 122.4, 122.1, 121.5, 120.5, 28.8, 25.5, 23.7.

To a flame dried Schlenk flask in a glovebox were added the sodium salt of 2-(2,6-di-i-propylanilino)tropone·THF (500 mg, 1.33 mmol) and (TMEDA)Ni(Ph)(Cl) (381 mg, 1.33 mmol). The flask was removed from the glovebox, was placed on a vacuum line under Ar, and was cooled with an ice water bath. Toluene (25 mL) and $CH_3CN$ (1.5 mL) were added to the flask, which was removed from the ice water bath after 30 min. The reaction was allowed to stir at ambient temperature for 14.5 h. Initial cannula filtration of the solution was followed by cannula transfer onto a pad of Celite and filtration under Ar. The Celite® pad was washed with toluene (20 mL), and the solvent volume was reduced in vacuo to 5 mL. Pentane (50 mL) was added, and the Schlenk flask was placed in a −30° C. freezer overnight. Solvent was removed from the precipitate via cannula filtration, and the residual solid was washed with pentane (5 mL). Drying in vacuo produced 90 mg (11%) of a red-brown solid. $^1H$ NMR (400 MHz, $C_6D_6$): δ 7.21–7.29 (m, 6H); 6.18–6.26 (m, 8H) 5.92 (m, 2H); 4.18 (sept, J=6.8 Hz, 4H); 1.74 (d, J=6.8 Hz, 12H); 1.19 (d, J=6.8 Hz, 12H).

What is claimed is:

1. A process for the polymerization of olefins, comprising the step of contacting, at a temperature of about −100° C. to about +200° C., one or more olefins with an active catalyst comprising a nickel complex of an anion of the formula

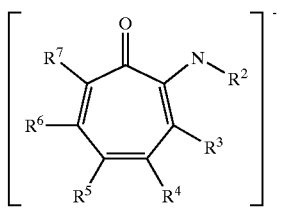

wherein:
- $R^2$ is hydrocarbyl or substituted hydrocarbyl, provided that $R^2$ is attached to said nitrogen atom in (I) by an atom that has at least 2 other atoms that are not hydrogen attached to it; and
- $R^3$, $R^4$, $R^5$, $R^6$ and $R^7$ are each independently hydrogen, hydrocarbyl, substituted hydrocarbyl or a functional group, provided that any two of $R^3$, $R^4$, $R^5$, $R^6$ and $R^7$ vicinal to one another may form a ring.

2. The process as recited in claim 1 wherein the olefin is selected from the group consisting of cyclopentene, a styrene, a norbornene, and compounds of the formula $R^{17}CH=CH_2$, wherein $R^{17}$ is hydrogen or alkyl.

3. The process as recited in claim 2 wherein the olefin is a compound of the formula $R^{17}CH=CH_2$.

4. The process as recited in claim 1 wherein said nickel complex is

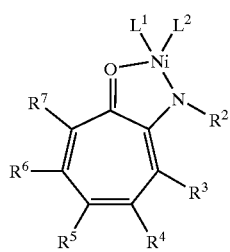

wherein:
- $L^1$ is a monodentate monoanionic ligand into which an olefin molecule may insert between $L^1$ and the nickel atom, and $L^2$ is an empty coordination site or a monodentate neutral ligand which may be displaced by an olefin, or $L^1$ and $L^2$ taken together are a monoanionic bidentate ligand into which an olefin may insert between said monoanionic bidentate ligand and said nickel atom;

and provided that when $L^1$ and $L^2$ taken together are

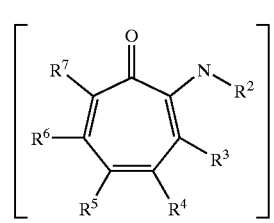

then a cocatalyst is also present.

5. The process as recited in claim 4 wherein $L^1$ and $L^2$ taken together are not (I).

6. The process as recited in claim 5 wherein the olefin is selected from the group consisting of cyclopentene, a styrene, a norbornene and compounds of the formulas $R^{17}CH=CH_2$, wherein $R^{17}$ is hydrogen or alkyl.

7. The process as recited in claim 6 wherein the olefin is a compound of the formula $R^{17}CH=CH_2$.

8. The process as recited in claim 1 wherein $R^2$ is

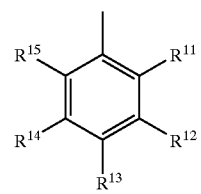

wherein $R^{11}$, $R^{12}$, $R^{13}$, $R^{14}$ and $R^{15}$ are each independently hydrogen, hydrocarbyl, substituted hydrocarbyl or a functional group, provided that any two of $R^{11}$, $R^{12}$, $R^{13}$, $R^{14}$ and $R^{15}$ vicinal to one another taken together may form a ring.

9. The process as recited in claim 5 wherein $R^2$ is

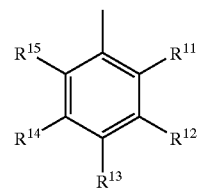

wherein $R^{11}$, $R^{12}$, $R^{13}$, $R^{14}$ and $R^{15}$ are each independently hydrogen, hydrocarbyl, substituted hydrocarbyl or a functional group, provided that any two of $R^{11}$, $R^{12}$, $R^{13}$, $R^{14}$ and $R^{15}$ vicinal to one another taken together may form a ring.

10. The process as recited in claim 9 wherein $R^{11}$ and $R^{15}$ are each independently chosen from the group consisting of alkyl containing 1 to 6 carbon atoms, perfluoroalkyl, alkoxy, phenyl and halo.

11. The process as recited in claim 10 wherein $R^{12}$, $R^{13}$ and $R^{14}$ are hydrogen.

* * * * *